(12) United States Patent
Akhondi et al.

(10) Patent No.: US 10,078,044 B2
(45) Date of Patent: Sep. 18, 2018

(54) METHOD AND ARRANGEMENT FOR DETERMINING AT LEAST ONE PORE-RELATED PARAMETER OF A POROUS MATERIAL

(71) Applicant: Nanyang Technological University, Singapore (SG)

(72) Inventors: Ebrahim Akhondi, Singapore (SG); William Bernard Krantz, Singapore (SG); Filicia Wicaksana, Singapore (SG); Anthony Gordon Fane, Singapore (SG)

(73) Assignee: Nanyang Technological University, Singapore (SG)

( * ) Notice: Subject to any disclaimer, the term of this patent is extended or adjusted under 35 U.S.C. 154(b) by 132 days.

(21) Appl. No.: 15/027,938

(22) PCT Filed: Oct. 3, 2014

(86) PCT No.: PCT/SG2014/000464
§ 371 (c)(1),
(2) Date: Apr. 7, 2016

(87) PCT Pub. No.: WO2015/053709
PCT Pub. Date: Apr. 16, 2015

(65) Prior Publication Data
US 2016/0252444 A1    Sep. 1, 2016

Related U.S. Application Data

(60) Provisional application No. 61/888,382, filed on Oct. 8, 2013, provisional application No. 61/899,533, filed on Nov. 4, 2013.

(51) Int. Cl.
*G01N 15/08* (2006.01)
*B01D 65/10* (2006.01)

(52) U.S. Cl.
CPC .......... *G01N 15/088* (2013.01); *B01D 65/10* (2013.01); *G01N 15/082* (2013.01)

(58) Field of Classification Search
CPC .. G01N 15/08; G01N 15/088; G01N 15/0893; G01N 15/082; G01N 15/0806;
(Continued)

(56) References Cited

U.S. PATENT DOCUMENTS

| 3,420,094 A | * | 1/1969 | Nyffenegger | ........ G01N 15/082 73/38 |
| 3,482,787 A | * | 12/1969 | Nyffenegger | ........... B02C 25/00 241/34 |
| 3,939,698 A | | 2/1976 | De Lacy | |
| 5,002,399 A | | 3/1991 | Akinc et al. | |

(Continued)

FOREIGN PATENT DOCUMENTS

| WO | WO 2011/137454 A1 | 11/2011 | |
| WO | WO 2011137454 A1 | * 11/2011 | ............... G01N 5/04 |

OTHER PUBLICATIONS

Extended European Search Report for corresponding European Application No. 14853122.1 dated May 9, 2017, 9 pages.
(Continued)

*Primary Examiner* — Peter Macchiarolo
*Assistant Examiner* — Nathaniel Kolb
(74) *Attorney, Agent, or Firm* — Alston & Bird LLP

(57) ABSTRACT

A method for determining at least one pore-related parameter of a porous material is provided. The method includes supplying a volatile liquid into a chamber, placing a porous material within the chamber, spaced apart from and over the volatile liquid, determining an effective mass of the chamber over a period of time, and determining at least one pore-related parameter of the porous material based on the effective mass determined. An arrangement for determining at least one pore-related parameter of a porous material is also provided.

13 Claims, 18 Drawing Sheets

(58) Field of Classification Search
CPC ....... G01N 2015/084; G01N 2015/086; B01D 65/10
USPC .......................................................... 73/38
See application file for complete search history.

(56) References Cited

U.S. PATENT DOCUMENTS

| | | | | |
|---|---|---|---|---|
| 6,789,410 | B1* | 9/2004 | Gupta | G01N 15/0826 73/38 |
| 9,618,441 | B2* | 4/2017 | Greenberg | G01N 15/0806 |
| 2003/0233865 | A1 | 12/2003 | Gupta et al. | |
| 2007/0148327 | A1* | 6/2007 | Baklanov | G01N 15/082 427/8 |
| 2013/0042670 | A1* | 2/2013 | Greenberg | G01N 5/04 73/38 |
| 2016/0051941 | A1* | 2/2016 | Li | B01D 53/228 96/4 |

OTHER PUBLICATIONS

Goh, S. et al., *Impact of a biofouling layer on the vapor pressure driving force and performance of a membrane distillation process*, Journal of Membrane Science, vol. 438 (2013) 140-152.

Krantz, W. et al., *Evapoporometry: A novel technique for determining the pore-size distribution of membranes*, Journal of Membrane Science, vol. 438 (2013) 153-166.

Takei, T. et al., *Validity of the Kelvin equation in estimation of small pore size by nitrogen adsorption*, Colloid Polymer Science., vol. 275 (1997) 1156-1161.

International Search Report and Written Opinion for International Application No. PCT/SG2014/000464, dated Dec. 23, 2014, 7 pages.

Akhondi, E. et al., *Evapoporometry Determination of Pore-Size Distribution and Pore Fouling of Hollow Fiber Membranes*, Journal of Membrane Science 470 (2014) 334-345.

* cited by examiner

METHOD AND ARRANGEMENT FOR DETERMINING AT LEAST ONE PORE-RELATED PARAMETER OF A POROUS MATERIAL

CROSS-REFERENCE TO RELATED APPLICATIONS

This application is a national phase entry of PCT/SG2014/000464, filed on 3 Oct. 2014, which claims the benefit of priority of U.S. provisional application No. 61/888,382, filed 8 Oct. 2013, and U.S. provisional application No. 61/899,533, filed 4 Nov. 2013, the contents of each being hereby incorporated by reference in their entirety for all purposes.

TECHNICAL FIELD

Various embodiments relate to a method for determining at least one pore-related parameter of a porous material and an arrangement for determining at least one pore-related parameter of a porous material.

BACKGROUND

Hollow fiber (HF) membranes that have a higher packing density than conventional flat sheet membranes and which readily permit backwashing are widely used in many applications. The pore sizes of microfiltration (MF) HF membranes range from 0.05 to 5 μm and those for ultrafiltration (UF) HF membranes range from 5 nm to 50 nm. Since the pore-size distribution (PSD) of membranes can greatly affect membrane performance, the PSD of HF membranes needs to be accurately characterized.

The PSD of UF membranes can be determined via direct observation methods such as scanning electron microscopy (SEM) and atomic force microscopy (AFM). SEM requires a high vacuum and therefore drying the sample, which can alter the pore structure. In order to minimize charging and damage due to the electron beam, non-conducting samples have to be conductively coated; this can decorate the membrane pores and alter the PSD. Field-emission SEM (FE-SEM) can reduce the charging and electron beam damage by being able to use a lower voltage. Environmental SEM (ESEM), developed for wet or non-conducting materials, avoids having to coat or dry the samples. However, lower resolution limits its use for characterizing UF membranes. AFM scans the sample surface with a fine tip on a cantilever whose deflections are used to generate a three-dimensional (3D) map of the surface topography. AFM does not require special sample preparation and can be done in a gas or liquid. It can determine the pore size, surface porosity, and PSD of a membrane. However, direct characterization methods image a small area (typically <1 mm$^2$) that might not be representative of the membrane on the macroscale. Furthermore, direct observation methods that include scanning electron microscopy (SEM), field-emission scanning electron microscopy (FESEM), environmental scanning electron microscopy (ESEM), and atomic force microscopy (AFM) require very expensive instruments that are limited in that they can measure the pore size only within a small area of a few hundred microns. Moreover, they are of limited use for obtaining the PSD of irregular pores such as encountered in solvent-cast polymeric membranes.

Indirect methods to determine the PSD based on the Young-Laplace equation relating the pressure to the pore diameter include liquid displacement porometry (LDP) and mercury porosimetry. LDP involves progressively displacing a nonvolatile wetting liquid from the largest to the smallest pores by a gas or immiscible liquid under pressure. The pore volume of a given diameter is determined from the displacing fluid flow rate at each pressure. The high pressure required by LDP for UF membranes (typically >30 bar) can cause compaction that alters the PSD and limits it to characterizing pores larger than approximately 10 nm. Mercury porosimetry involves progressively filling the pores with mercury and uses a data-analysis procedure similar to LDP. The PSD determined by mercury porosimetry includes dead-end and continuous pores in contrast to LDP that measures only continuous pores. Owing to the high surface tension of mercury, this technique requires very high pressures.

Indirect methods based on the Kelvin equation relating the vapor pressure to the pore diameter include gas adsorption/desorption (GAD) and permporometry. Both methods involve filling the pores via adsorption and capillary condensation and then reducing the partial pressure to cause progressive desorption from the largest to the smallest pores; the pore volume for each diameter is determined from the amount of gas desorbed. Whereas the PSD determined by GAD includes both continuous pores that extend through the membrane and dead-end pores, permporometry determines only the continuous pores by imposing the simultaneous flow of a non-condensable gas during pore draining. A concentration or temperature gradient can be the driving force for the non-condensable gas flow. Using permporometry is challenging especially for HF membranes because it is necessary to control and measure the non-condensable carrier gas and condensable gas flow rates and the partial pressures across the membrane as well as the temperature. The PSD determined by GAD and permporometry has to be corrected for the t-layer (typically <1 nm). A t-layer forms owing to equilibrium adsorption of gas on the pore walls. The resulting thin adsorbed layer has a maximum thickness on the order of a few nanometers that depends on the particular gas and its partial pressure.

Techniques such as displacement porometry (LDP) and gas adsorption/desorption require relatively expensive dedicated equipment. LDP involves the application of high pressures that can deform the material and thereby its pore-size distribution. Moreover, displacement porometry can characterize only relatively large pores typically greater than 0.01 microns. Gas adsorption/desorption can accurately characterize only relatively small pores typically less than 0.01 microns.

Indirect methods based on the Gibbs-Thompson equation relating the freezing-point temperature to the pore diameter include thermoporometry. This involves gradually increasing the temperature of a frozen liquid-saturated membrane that causes melting progressively from the smallest to the largest pores. The pore diameter and the associated pore volume are obtained from the heat released during solidification or the heat input during melting. A correction is necessary for the smallest pores due to a submicron layer of unfrozen liquid at the pore walls (similar to the t-layer in GAD and permporometry).

SUMMARY

According to an embodiment, a method for determining at least one pore-related parameter of a porous material is provided. The method may include supplying a volatile liquid into a chamber, placing a porous material within the chamber, spaced apart from and over the volatile liquid, determining an effective mass of the chamber over a period of time, and determining at least one pore-related parameter of the porous material based on the effective mass determined.

According to an embodiment, an arrangement for determining at least one pore-related parameter of a porous material is provided. The arrangement may include a porous material, a chamber configured to receive a volatile liquid, the chamber including a support structure, wherein the porous material is received by the support structure to be arranged spaced apart from and over the volatile liquid, and a mass determination device upon which the chamber is to be positioned.

BRIEF DESCRIPTION OF THE DRAWINGS

In the drawings, like reference characters generally refer to like parts throughout the different views. The drawings are not necessarily to scale, emphasis instead generally being placed upon illustrating the principles of the invention. In the following description, various embodiments of the invention are described with reference to the following drawings, in which:

FIG. 7A shows the PSD uncorrected for the nonzero contact angle of water on PAN; FIG. 7B shows the PSD based on the same raw data corrected for the nonzero contact angle of water on PAN.

FIG. 8A shows the PSD uncorrected for the nonzero contact angle of water on PVDF; FIG. 8B shows the PSD based on the same raw data corrected for the nonzero contact angle of water on PVDF.

FIG. 10B is corrected for the contact angle of water on PVDF.

DETAILED DESCRIPTION

Figure 1A:
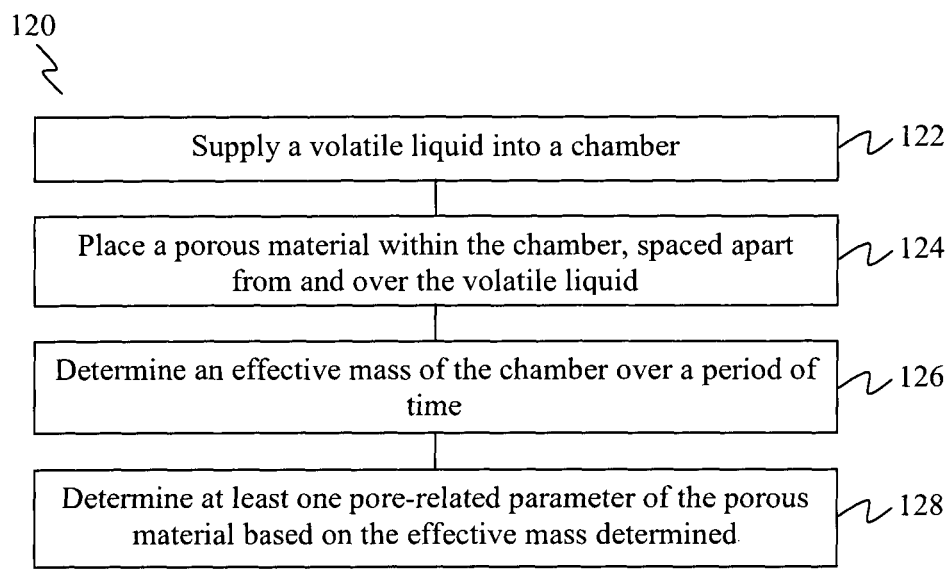
FIG. 1A shows a flow chart illustrating a method for determining at least one pore-related parameter of a porous material, according to various embodiments.

The following detailed description refers to the accompanying drawings that show, by way of illustration, specific details and embodiments in which the invention may be practiced. These embodiments are described in sufficient detail to enable those skilled in the art to practice the invention. Other embodiments may be utilized and structural, logical, and electrical changes may be made without departing from the scope of the invention. The various embodiments are not necessarily mutually exclusive, as some embodiments can be combined with one or more other embodiments to form new embodiments.

Embodiments described in the context of one of the methods or devices are analogously valid for the other methods or devices. Similarly, embodiments described in the context of a method are analogously valid for a device, and vice versa.

Features that are described in the context of an embodiment may correspondingly be applicable to the same or similar features in the other embodiments. Features that are described in the context of an embodiment may correspondingly be applicable to the other embodiments, even if not explicitly described in these other embodiments. Furthermore, additions and/or combinations and/or alternatives as described for a feature in the context of an embodiment may correspondingly be applicable to the same or similar feature in the other embodiments.

In the context of various embodiments, the articles "a", "an" and "the" as used with regard to a feature or element include a reference to one or more of the features or elements.

In the context of various embodiments, the phrase "at least substantially" may include "exactly" and a reasonable variance.

In the context of various embodiments, the term "about" or "approximately" as applied to a numeric value encompasses the exact value and a reasonable variance.

As used herein, the term "and/or" includes any and all combinations of one or more of the associated listed items.

As used herein, the phrase of the form of "at least one of A or B" may include A or B or both A and B. Correspondingly, the phrase of the form of "at least one of A or B or C", or including further listed items, may include any and all combinations of one or more of the associated listed items.

Various embodiments may relate to an apparatus and a method for determining the porosity, pore size, pore-size distribution, and internal pore fouling of hollow fibers and tubular shape materials (e.g., tubular membranes). Various embodiments may also relate to the design and application of a suitable test cell for characterization of hollow fibers and tubular membranes.

Various embodiments may provide a technique for characterization of hollow fibers and tubular membranes, and membrane internal fouling, for example relating to at least one pore-related parameter of the membranes.

Various embodiments may enable determination of the porosity, pore-size distribution, and internal pore fouling of hollow fibers and tubular shape materials (e.g., tubular membranes) by evaporative mass loss. For example, various embodiments may provide evapoporometry determination of the porosity, pore-size distribution and pore fouling of hollow fiber membranes.

Various embodiments may provide an approach or technique for determining the pore-size distribution (PSD) on the outer side of tubular porous materials, for example, hollow fibers, capillary and tubular membranes.

Evapoporometry (EP) is an indirect method that is based on the Kelvin equation that may relate the reduction in vapor pressure of a wetting liquid to the pore diameter. EP may involve placing the porous samples that may be pre-saturated with a volatile wetting liquid in a specially designed chamber or test cell that may be placed on a microbalance in order to determine the evaporation rate.

As examples, using EP, characterization of Anopore flat sheet membranes with a regular non-interconnected columnar pore geometry may provide a mass-average pore diameter that may agree well with the 100 nm nominal pore diameter provided by the manufacturer, FESEM analysis, and a previously determined mean-flow pore diameter. Furthermore, EP characterization of commercial 20 and 50 nm polyvinylidene fluoride (PVDF) flat sheet membranes may agree well with the nominal pore size. However, the diameter determined by EP may be larger than that determined by LDP, which may be attributed to membrane compaction caused by the high applied pressure used in LDP.

EP offers several advantages over the current techniques (e.g., direct and other indirect methods) for determining pore size and pore-size distribution (PSD). EP may characterize a large membrane area relative to that characterized by SEM, FESEM and AFM. Low cost and a small laboratory footprint are also advantages of EP relative to indirect observation techniques such as LDP. EP requires only multi-purpose laboratory equipment such as a microbalance, an environmental chamber and an anti-vibration table, all of which may be readily available. EP may directly determine the mass-based pore-size distribution (PSD) of the membranes from the evaporation rates that may not be particularly sensitive to either the measurement conditions or the test cell dimensions. EP may have a higher accuracy than methods that require measuring quantities such as volumetric flow rates, partial pressures, or differential heat input. This technique may not require assuming any model for the pore geometry other than a circular cross-section of the pores at the surface of the membrane, which may not be particularly limiting. EP may be used to determine the PSD of a biofouling layer, where modeling studies show that the pore diameters determined using EP may explain the anomalous reduction in permeation flux observed in membrane distillation owing to biofouling.

EP may be used to characterize the PSD for flat sheet membranes. While water may be used as the volatile wetting liquid in adapting EP to determine the PSD of viable biofouling layers, it should be appreciated that different liquids may be used for determination of the PSD of samples. Furthermore, while EP may be used for determining the PSD of 'clean' membranes, it should be appreciated that EP may also be able to provide useful information on internal pore fouling. In various embodiments, EP may be adapted to permit characterizing the PSD of HF membranes. The ability of EP to characterize the PSD of commercial HF membranes using both isopropyl alcohol (IPA) and water may be demonstrated as will be described later below. An application of EP to assess internal pore fouling of HF membranes may be possible, as will also be described later below.

In various embodiments, evapoporometry (EP) may permit characterizing pore sizes from a few nanometers up to near micron-scale by measuring the mass loss as a function of time from the porous material that is contained within an appropriately designed chamber or test cell by using a microbalance or that is integrated with a suitable device to provide instantaneous accurate weighing at the microgram ($\mu$g) level.

In various embodiments, it may be necessary to characterize the pore size and pore-size distribution (PCD) of hollow fibers and tubular samples (e.g., tubular membranes) in many applications. Evapoporometry (EP) may be used in order to determine the pore size and the porosity based on the evaporative mass loss from porous materials that may be pre-saturated with a wetting volatile liquid. The vapor pressure of the wetting liquid may be reduced owing to the effects of surface curvature at the interface of a liquid within the pores. This technique may involve placing the porous samples that may have been saturated with a volatile wetting liquid in an appropriate chamber or test cell that may be placed on a microbalance or that is integrated with a suitable device to provide instantaneous accurate weighing at the microgram ($\mu$g) level. The chamber or test cell may permit the vapor at the membrane surface to be saturated with respect to the liquid in the pore size that is draining. The microbalance may be used for measuring the mass as a function of time. The slope of the mass versus time curve may be the evaporation rate. The evaporation rate may be related to the mole fraction of the wetting liquid at the interface between the liquid in the pores and the ambient gas phase. The mole fraction may be related to the pore diameter. The liquid may evaporate progressively from the largest pores down to the smallest pores since the vapor pressure decreases with decreasing pore diameter for a wetting liquid. At any instant of time, liquid may be evaporating from only one pore size since the ambient gas phase environment above any smaller pores may be supersaturated, whereas any larger pores may already have been emptied.

In various embodiments, evapoporometry (EP) may determine the pore diameter from the vapor-pressure depression that occurs for a wetting liquid in small pores. EP is based on evaporating a wetting volatile liquid from a porous material under conditions for which the gas at the membrane surface may be saturated with respect to the liquid in the pore size that is draining, but supersaturated with respect to all smaller pores. Hence, evaporation may progress from the largest to the smallest pores. No evaporation may occur from smaller pores when evaporation is occurring from any larger pore as the ambient gas phase next to the volatile liquid in the smaller pores may be supersaturated. This may mean that, as the vapor-pressure depression may increase as the pore diameter decreases, evaporation of a volatile wetting liquid from a membrane under conditions of uniform saturation over its surface may progress in time from the largest to the smallest pores; that is, at any instant of time the vapor next to the membrane surface may be saturated with respect to the pores that are being emptied owing to evaporation, but supersaturated with respect to all smaller pores for which no liquid loss may be occurring.

The Kelvin equation may be used to obtain the pore diameter, d, from the instantaneous vapor pressure for a wetting liquid or solvent, as provided below:

$$\ln \frac{\bar{p}_A}{p_A^\circ} = -\frac{4V\sigma\cos\theta}{dRT}, \quad \text{(Equation 1)}$$

where $p_A^\circ$ is the vapor pressure of the volatile wetting liquid (or volatile solvent/liquid) over a flat interface, $\bar{p}_A$ is the instantaneous partial pressure of the wetting liquid (or solvent) in the pores that are draining, $\sigma$ is the interfacial tension, V is the liquid molar volume, R is the gas constant, T is the absolute temperature and $\theta$ is the contact angle.

For a completely wetting liquid for which $\theta=0$, Equation 1 may be written as $$\ln \frac{\bar{p}_A}{p_A^\circ} = -\frac{4\sigma V}{dRT}, \quad \text{(Equation 2)}$$

and may assume the following form:

$$d = -\frac{4\sigma V}{RT\ln\frac{\bar{p}_A}{p_A^\circ}}, \quad \text{(Equation 3)}$$

Equation 3 may be expressed in terms of mole fractions as below:

$$d = -\frac{4\sigma V}{RT\ln\frac{x_{A0}}{x_{A0}^\circ}}, \quad \text{(Equation 4)}$$

where $x_{A0}$ is the mole fraction at the surface of a membrane during liquid loss owing to evaporation (or during pore draining) and $x_{A0}^\circ$ is the mole fraction at the surface of a planar liquid layer (or the mole fraction at the surface of an evaporating free-standing liquid layer). The applicability of the Kelvin equation for diameters as small as 8 nm, as well as for a lower bound of 4 nm have been reported.

The Kelvin equation given by Equation 1 may be inaccurate for pore diameters less than approximately 4 nm. Further, the vapor-pressure depression may become quite small for pores larger than approximately 150 nm. Equation 3 assumes a circular liquid-gas interface within the pore at the surface of the membrane, which assumption may not be particularly limiting. The model used to extract $x_{A0}$, the mole fraction at the surface of the membrane, from the instantaneous evaporation rate assumes one-dimensional steady-state mass transfer. One-dimensional mass transfer may require that the distance between adjacent pores be much less than L, being the length of a chamber or test cell, which may be satisfied if $$\frac{1-\varepsilon}{n_p L^2} \ll 1, \quad \text{(Equation 5)}$$

where $\varepsilon$ is the porosity of the porous sample and $n_p$ is the number of pores per unit area. Satisfying Equation 5 may also ensure that the vapor pressure may be uniform across the surface of the membrane. The criteria for assuming steady-state are provided as below:

$$\frac{D_{AB}t}{L^2} \gg 1, \quad \text{(Equation 6)}$$

$$Vc \ll 1, \quad \text{(Equation 7)}$$

where $D_{AB}$ is the binary diffusivity for the volatilized liquid in air, t is the contact time and c is the molar density of the gas phase.

The vapor-pressure depression upon which EP is based may be determined by the pore diameter at the membrane surface. If the functional side of the membrane with the smaller pores is facing upward (e.g., into the gas phase), evaporation may cause the pores to empty from the bottom upwards. However, pore constrictions or interconnectivity may cause the liquid-gas interface to recede into the pore until the curvatures may be equal at the top and bottom of the liquid column in the pore. Hence, some of the liquid in pores having a larger pore diameter at the membrane surface may be attributed to smaller pores, which may cause a shift of the PSD to smaller pore diameters. EP requires that the volatile wetting liquid not react or swell the membrane. Moreover, the vapor pressure of ambient air should be carefully controlled during EP, which may be challenging when water is used as the volatile wetting liquid.

FIG. 1A shows a flow chart 120 illustrating a method for determining at least one pore-related parameter of a porous material, according to various embodiments.

At 122, a volatile liquid is supplied into a chamber. For example, a predetermined amount or volume (e.g., approximately 0.5 ml) of the volatile liquid may be supplied into the chamber.

At 124, a porous material (or porous sample) is placed within the chamber, spaced apart from and over the volatile liquid. For example, the porous material may be supported or received by a support structure within the chamber. This may mean that the support structure may be spaced apart from and over the volatile liquid. As non-limiting examples, the porous material may be a porous tubular or hollow fiber material. In various embodiments, the porous material may include the volatile liquid.

At 126, an effective mass of the chamber is determined over a period of time. For example, the effective mass of the chamber may be determined using a mass determination device, where the chamber may be positioned on the mass determination device.

At 128, at least one pore-related parameter (e.g., pore diameter) of the porous material is determined based on the effective mass (or effective masses) determined.

It should be appreciated that the porous material may include a plurality of pores of one or more sizes/diameters.

In the context of various embodiments, the pore-related parameter of the porous material may be related to the porosity, the pore size, the pore-size distribution, or the internal pore fouling of the porous material.

In the context of various embodiments, the mass determination device may be or may include a microbalance or a device capable of providing instantaneous accurate weighing at the microgram level.

In various embodiments, the method may further include determining an evaporation rate from the effective mass determined, relating the evaporation rate to a vapor pressure of the volatile liquid at an interface between the volatile liquid in the porous material and an ambient gas phase within the chamber, and wherein at 128, the at least one pore-related parameter may be determined based on the vapor pressure determined.

In various embodiments, the method may further include determining an evaporation rate from the effective mass determined, relating the evaporation rate to a mole fraction of the volatile liquid at an interface between the volatile liquid in the porous material and an ambient gas phase within the chamber, and wherein at 128, the at least one pore-related parameter may be determined based on the mole fraction determined.

In various embodiments, at 126, the effective mass of the chamber may be determined at a series of time intervals.

In various embodiments, a start of a pore-liquid evaporation period (e.g., pore draining period) may be determined prior to determining an effective mass of the chamber. For example, this may include determining a porosity of the porous material, and determining, based on the determined porosity, a mass of the volatile liquid in the porous material (e.g., a mass of the volatile liquid in the pores of the porous material).

In various embodiments, the method may further include determining a contact angle between the porous material and the volatile liquid in the porous material, and wherein at 128, the method may further include modifying the determined at least one pore-related parameter according to the contact angle determined.

In various embodiments of the method, the at least one pore-related parameter may be a pore-size distribution, wherein at 126, the effective mass of the chamber may be determined at a series of time intervals to generate a plurality of instantaneous masses, and wherein at 128, a respective instantaneous mass of the determined plurality of instantaneous masses may be related to a respective pore diameter of the porous material, and the pore-size distribution may be determined based on the instantaneous masses determined and the associated pore diameters.

In various embodiments, the method may further include introducing or providing the volatile liquid to the porous material. For example, a predetermined amount or volume of the volatile liquid may be provided to the porous material. The volatile liquid may be provided to the porous material prior to placing the porous material in the chamber or when the porous material is within the chamber. Providing the volatile liquid to the porous material may include saturating the porous material with the volatile liquid.

In various embodiments, the method may further include saturating the porous material with the volatile liquid. In various embodiments, the method may include saturating the porous material with the volatile liquid prior to placing the porous material in the chamber. In other words, the porous material may be pre-saturated with the volatile liquid. For example, this may be carried out by immersing the porous material in the volatile liquid (e.g., a wetting liquid) for a predetermined duration of time (e.g., for a few hours or overnight). In various embodiments, the method may include saturating the porous material within the chamber with the volatile liquid. This may mean that the porous material may be saturated while the porous material is within the chamber.

In various embodiments, at 122, the volatile liquid may be supplied to a base portion of the chamber, and at 124, the porous material may be arranged spaced apart from and over the base portion.

In various embodiments, the method may further include controlling evaporation (e.g., evaporation rate) of the volatile liquid in the chamber. For example, this may be achieved by arranging a diffusional resistance element spaced apart from and over the porous material, wherein the diffusional resistance element may be configured to resist diffusion of vapor of the volatile liquid.

In various embodiments, the diffusional resistance element may include a microporous membrane or a microporous filter arranged spaced apart from and over the porous material. The microporous membrane or the microporous filter may be provided in a holder. The microporous membrane or the microporous filter may be arranged within the chamber or configured as a cap (or lid) to be arranged over a top of the chamber. The microporous membrane or the microporous filter may be removable. This may be helpful so as to allow the porous material to be placed in the chamber to be characterized by EP and to allow the porous material to be removed thereafter. The microporous membrane or the microporous filter may have a pore size between about 0.1 μm and about 100 μm, for example, between about 0.1 μm and about 50 μm, between about 0.1 μm and about 20 μm, between about 0.1 μm and about 10 μm, between about 1 μm and about 10 μm, between about 1 μm and about 50 μm, between about 10 μm and about 100 μm, or between about 50 μm and about 100 μm. In various embodiments, the microporous membrane or the microporous filter may include a material selected from the group consisting of polytetrafluoroethylene, polyethylene, polypropylene, polydimethylsiloxane, polyvinylidene fluoride, and poly(ethylene chlorotrifluoroethylene. However, it should be appreciated that other materials may also be used.

In various embodiments, the diffusional resistance element may include a covering structure arranged spaced apart from and over the porous material, the covering structure having a hole (e.g., a vent hole). The covering structure may be arranged within the chamber or configured as a cap (or lid) to be arranged over a top of the chamber. The covering structure may be removable. This may be helpful so as to allow the porous material to be placed in the chamber to be characterized by EP and to allow the porous material to be removed thereafter. A diameter of the hole of the covering structure may be between about 0.1 cm (1 mm) and about 10 cm, for example, between about 0.1 cm and about 5 cm, between about 0.1 cm and about 1 cm, between about 1 cm and about 10 cm, between about 1 cm and about 5 cm, or between about 5 cm and about 10 cm.

In various embodiments, the diffusional resistance element may include a layer of fibrous material such as a layer of fiberglass arranged within the chamber, spaced apart from and over the porous material. The layer of fiberglass may be arranged over but not touching the porous material so as to control the evaporation rate. The layer of fiberglass may be arranged approximately 1 mm over or above the porous material.

In the context of various embodiments, at 124, a porous material (e.g., a porous tubular or hollow fiber material) may be placed within the chamber, spaced apart from and over the volatile liquid, and a layer of fibrous material such as fiberglass may be placed over but not touching the porous material to control the evaporation rate.

It should be appreciated that the diffusional resistance element may include the membrane or the covering structure or the layer of fiberglass, or an arrangement having at least one of the membrane, the covering structure, or the layer of fiberglass.

In various embodiments, the method may further include maintaining the chamber at an at least substantially constant temperature. For example, this may be achieved by positioning the chamber within an incubator (or an environmental chamber).

In various embodiments, the method may further include monitoring (or measuring) a temperature of the environment the chamber is exposed to. The temperature may be continuously monitored. For example, the temperature in the incubator or the environmental chamber may be monitored.

In various embodiments, the method may further include monitoring (or measuring) a humidity of the environment the chamber is exposed to. The humidity may be continuously monitored. For example, the humidity in the incubator or the environmental chamber may be monitored. In various embodiments, the humidity of the environment the chamber is exposed to may be controlled. For example, this may be achieved by means of an adsorbent material (e.g., a silica gel).

In various embodiments, the method may further include controlling a vapor concentration of the volatile liquid within the chamber. For example, this may be achieved by means of an adsorbent material (e.g., a silica gel).

In various embodiments, the method may further include mitigating or eliminating static charges. For example, this may be achieved by positioning or arranging a material, device, or mechanism within the chamber or housing of the mass determination device (e.g., a microbalance or other device capable of measuring the mass on the microgram level) to mitigate or eliminate static charges, which otherwise may compromise the accuracy of the mass determination device (e.g., a microbalance). The static mitigating material, device, or mechanism may be a Polonium (Po) source. This may be necessary when performing evapoporometry (EP) in a dry climate and/or a non-humid environment.

In various embodiments, the method may further include exposing the porous material to a foulant.

In the context of various embodiments, the porous material may include one or a plurality of tubular porous materials. A tubular porous material may include a hollow fiber membrane, a capillary membrane or a tubular membrane.

In various embodiments, each tubular porous material may be arranged horizontally, for example this may mean that a longitudinal axis of each tubular porous material may be at least substantially parallel to a surface (e.g., top surface) of the volatile liquid.

In various embodiments, the method may further include sealing opposite ends (e.g., lumen ends) of each tubular porous material. For example, the opposite ends may be heat-sealed.

In various embodiments, the porous material may include a plurality of tubular porous materials, where the method may further include laying the plurality of tubular porous materials side-by-side. For example, the plurality of tubular porous materials may be arranged along a plane (e.g., a horizontal plane) at least substantially parallel to a surface (e.g., top surface) of the volatile liquid. The method may further include arranging the plurality of tubular porous materials spaced apart from each other. In the context of various embodiments, the plurality of tubular porous materials may be spaced apart from each other by a spacing of between about 0.5 mm and about 1 mm, for example between about 0.5 mm and about 0.8 mm or between about 0.7 mm and about 1 mm, e.g., about 1 mm.

In the context of various embodiments, each tubular porous material may include a hollow fiber (HF) membrane.

In the context of various embodiments, the porous material may include an at least substantially flat porous material, e.g., a flat membrane.

In the context of various embodiments, the volatile liquid may be a wetting volatile liquid.

In the context of various embodiments, the volatile liquid may be a non-wetting volatile liquid.

In the context of various embodiments, the volatile liquid may produce vapor that is less dense than air, e.g., water.

In the context of various embodiments, the volatile liquid may produce vapor that is more dense than air, e.g., isopropyl alcohol (IPA).

While the method described above is illustrated and described as a series of steps or events, it will be appreciated that any ordering of such steps or events is not to be interpreted in a limiting sense. For example, some steps may occur in different orders and/or concurrently with other steps or events apart from those illustrated and/or described herein. In addition, not all illustrated steps may be required to implement one or more aspects or embodiments described herein. Also, one or more of the steps depicted herein may be carried out in one or more separate acts and/or phases.

Figure 1B:
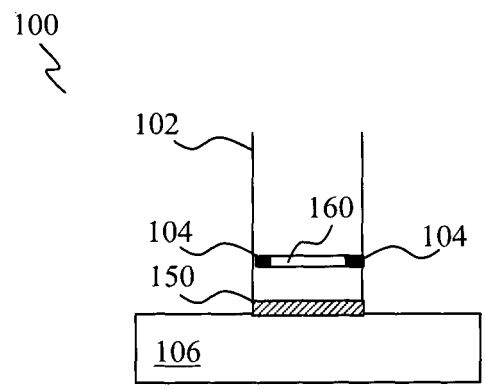
FIG. 1B shows a schematic cross-sectional view of an arrangement for determining at least one pore-related parameter of a porous material, according to various embodiments.

FIG. 1B shows a schematic cross-sectional view of an arrangement 100 for determining at least one pore-related parameter of a porous material, according to various embodiments. The arrangement 100 includes a porous material 160, a chamber (or test cell) 102 configured to receive a volatile liquid 150, the chamber 102 including a support structure (e.g., one or more clamps or clips) 104, wherein the porous material 160 is received by the support structure 104 to be arranged spaced apart from and over the volatile liquid 150, and a mass determination device 106 upon which the chamber 102 is to be positioned.

In other words, the arrangement 100 may include a chamber 102 adapted to receive a volatile liquid 150. The volatile liquid 150 may form a liquid layer (e.g., a free-standing liquid layer). The chamber 102 may include a support structure 104, which may receive or support a porous material (or porous sample) 160. The porous material 160 may include a plurality of pores of one or more sizes (or diameters). The porous material 160 may include or be saturated with a volatile liquid, for example, the same as the volatile liquid 150. The porous material 160 may be received or supported by the support structure 104 such that the porous material may be arranged separated from the volatile liquid 150 received by the chamber 102. In other words, the porous material 160 arranged in the chamber 102 may not be in contact with the volatile liquid 150 received by the chamber 102. Accordingly, the porous material 160 supported by the support structure 104 may be arranged elevated relative to the volatile liquid 150 received by the chamber 102. The support structure 104 may also be arranged separated from the volatile liquid 150 received by the chamber 102.

By placing the porous material 160 over the volatile liquid 150, the volatile liquid 150 may evaporate and the resulting vapor may diffuse towards the porous material 160. In vapor may not diffuse through the porous material 160. In embodiments where the porous material 160 may include a plurality of tubular porous materials (e.g., hollow fiber (HF)

membranes, capillary membranes or tubular membranes) spaced apart from each other, the vapor may pass through the spacing between adjacent tubular porous materials.

By placing the porous material 160 spaced apart from the volatile liquid 150, formation of meniscus between the porous material 160 and the volatile liquid 150 may be avoided.

The arrangement 100 may further include a mass determination device 106, where the chamber 102, including the porous material 160 as supported by the support structure 104, may be positioned on the mass determination device 106. The mass determination device 106 may record mass or a change in mass. For example, the mass determination device 106 may be configured to determine an effective mass of the chamber 102 as a function of time. In this way, an effective mass of the porous material 160 may also be determined.

In the context of various embodiments, the effective mass of the chamber 102 may include the mass of the chamber 102 and the mass of its contents.

In the context of various embodiments, the effective mass of the porous material 160 may include the mass of the porous material 160 and the mass of the volatile liquid presents in the pores of the porous material 160.

In various embodiments, the arrangement 100 may further include a diffusional resistance element arranged spaced apart from and over the porous material 160, wherein the diffusional resistance element may be configured to resist diffusion of vapor of the volatile liquid 150 so as to control evaporation (e.g., evaporation rate) of the volatile liquid 150. The diffusional resistance element may also be arranged spaced apart from and over the support structure 104. In various embodiments, the diffusional resistance element may be required when the volatile liquid 150 used is water, which may cause free convection mass transfer, or isopropyl alcohol (IPA). Nevertheless, it should be appreciated that the diffusional resistance element may also be provided when other volatile liquids are used.

The diffusional resistance element may include an inert material that may not react with the vapor of the volatile liquid 150, e.g., water vapor or vapor of isopropyl alcohol (IPA)), meaning inert (e.g., chemically inert) to the vapor of the volatile liquid 150.

In various embodiments, the diffusional resistance element may include a microporous membrane or a microporous filter. The microporous membrane or the microporous filter may be provided in a holder. The microporous membrane or the microporous filter may be arranged within the chamber 102 or configured as a cap (or lid) to, be arranged over a top of the chamber 102. The microporous membrane or the microporous filter may be removable. The microporous membrane or the microporous filter may have a pore size between about 0.1 µm and about 100 µm, for example, between about 0.1 µm and about 50 µm, between about 0.1 µm and about 20 µm, between about 0.1 µm and about 10 µm, between about 1 µM and about 10 µm, between about 1 µm and about 50 µm, between about 10 µm and about 100 µm, or between about 50 µm and about 100 µm. In various embodiments, the microporous membrane or the microporous filter may include a material selected from the group consisting of polytetrafluoroethylene, polyethylene, polypropylene, polydimethylsiloxane, polyvinylidene fluoride, and poly(ethylene chlorotrifluoroethylene. However, it should be appreciated that other materials may also be used.

In various embodiments, the diffusional resistance element may include a covering structure having a hole (e.g., a vent hole). The covering structure may be arranged within the chamber 102 or configured as a cap (or lid) to be arranged over a top of the chamber 102. The covering structure may be removable. A diameter of the hole of the covering structure may be between about 0.1 cm (1 mm) and about 10 cm, for example, between about 0.1 cm and about 5 cm, between about 0.1 cm and about 1 cm, between about 1 cm and about 10 cm, between about 1 cm and about 5 cm, or between about 5 cm and about 10 cm.

In various embodiments, the diffusional resistance element may be or may include a layer of fiberglass arranged within the chamber 102. In various embodiments, the layer of fiberglass may be arranged approximately 1 mm above the support structure 104 or the porous material 160. In the context of various embodiments, the layer of fiberglass may have a thickness in a range of between about 1 cm and about 10 cm, for example, between about 1 cm and about 5 cm, between about 1 cm and about 3 cm, between about 5 cm and about 10 cm, or between about 3 cm and about 7 cm.

It should be appreciated that the diffusional resistance element may include the membrane or the covering structure or the layer of fiberglass, or an arrangement having at least one of the membrane, the covering structure, or the layer of fiberglass.

In various embodiments, the chamber 102 may include a base portion configured to receive the volatile liquid 150, and wherein the porous material 160 may be arranged spaced apart from and over the base portion. This may mean that the porous material 160 supported by the support structure 104 may be arranged elevated relative to the base portion. Further, the support structure 104 may be arranged spaced apart from and over the base portion. The base portion may include aluminum (Al). In various embodiments, the base portion may have a reservoir configured to receive the volatile liquid 150.

In various embodiments, an end of the chamber 102 that is distal to the base portion may be an open end. This may mean that the chamber 102 may have an open top.

In various embodiments, a length of between about 5 cm and about 10 cm may be defined between the open end and the porous material 160. For example, the length between the open end and the porous material 160 may be between about 5 cm and about 8 cm or between about 7 cm and about 10 cm. The lengths described here may also define the length of the chamber 102.

In various embodiments, the chamber 102 may further include an upper portion removably coupled to the base portion, e.g., by means of bolts and nuts. The upper portion of the chamber 102 may include Teflon or any suitable low energy material that may minimize or avoid the volatile liquid 150 from wetting the wall of the upper portion.

In various embodiments, the chamber 102 may include a low energy material (e.g., Teflon) adapted to minimize (or avoid) wetting by the volatile liquid 150.

In the context of various embodiments, the chamber 102 may have a cross-sectional dimension (e.g., diameter) in a range of between about 3 cm and about 10 cm, for example, between about 3 cm and about 7 cm, between about 3 cm and about 5 cm, or between about 4 cm and about 10 cm, e.g., about 4 cm.

The arrangement 100 may further include an incubator or an environmental chamber within which the chamber 102 is to be positioned so as to maintain an at least substantially constant temperature within the chamber 102.

The arrangement 100 may further include a temperature sensor arranged within the incubator or the environmental chamber.

The arrangement 100 may further include a humidity sensor arranged within the incubator or the environmental chamber.

The arrangement 100 may further include an adsorbent material arranged within the incubator or the environmental chamber, the adsorbent material configured to adsorb at least one of vapor of the volatile liquid 150 (so as to control the vapor concentration of the volatile liquid) within the chamber 102 (and the incubator/environmental chamber) or moisture within the chamber 102 (and the incubator/environmental chamber). The adsorbent material may be a dehumidification material, meaning that the adsorbent material may provide a dehumidification function or may function as a dehumidifier. The adsorbent material may be or may include a silica gel.

The arrangement 100 may further include a material, device, or mechanism positioned within the chamber or housing of the mass determination device 106 (e.g., a microbalance or other device capable of measuring the mass on the microgram level) to mitigate or eliminate static charges, which otherwise may compromise the accuracy of the mass determination device 106 (e.g., a microbalance). The static mitigating material, device, or mechanism may be a Polonium (Po) source. This may be necessary when performing evapoporometry (EP) in a dry climate and/or a non-humid environment.

The arrangement 100 may further include an anti-vibration platform upon which the mass determination device 106 is to be supported. The anti-vibration platform may be an anti-vibration table.

In various embodiments, the porous material 160 may be saturated (e.g., pre-saturated) with the volatile liquid 150.

In various embodiments, the porous material 160 may include one or a plurality of tubular porous materials. Each tubular porous material may include a hollow fiber (HF) membrane, a capillary membrane or a tubular membrane. Opposite ends (e.g., lumen ends) of each tubular porous material may be sealed, e.g., by means of heat-sealing.

In various embodiments, the porous material 160 may include a plurality of tubular porous materials, where the plurality of tubular porous materials may be arranged side-by-side. The plurality of tubular porous materials may be arranged spaced apart from each other. In the context of various embodiments, the plurality of tubular porous materials may be spaced apart from each other by a spacing of between about 0.5 mm and about 1 mm, for example, between about 0.5 mm and about 0.8 mm or between about 0.7 mm and about 1 mm.

In various embodiments, each tubular porous material may include a hollow fiber (HF) membrane.

In various embodiments, the porous material 160 may include an at least substantially flat porous material, e.g., a flat membrane.

In the context of various embodiments, the chamber 102 may be a cylindrical chamber. In the context of various embodiments, the chamber 102 may have a circular cross-section. However, it should be appreciated that other cross-sectional shapes may be employed.

In the context of various embodiments, the pore-related parameter of the porous material may refer to the porosity, the pore size, the pore-size distribution, or the internal pore fouling of the porous material 160.

In the context of various embodiments, the mass-determination device 106 may be or may include a microbalance or a device capable of providing instantaneous accurate weighing at the microgram (μg) level.

In the context of various embodiments, the volatile liquid 150 may be a wetting volatile liquid.

In the context of various embodiments, the volatile liquid 150 may be a non-wetting volatile liquid.

In the context of various embodiments, the volatile liquid 150 may produce vapor that is less dense than air, e.g., water.

In the context of various embodiments, the volatile liquid 150 may produce vapor that is more dense than air, e.g., isopropyl alcohol (IPA).

In the context of various embodiments, the term "tubular porous material" may include a membrane having a tubular shape, and may be sub-classified into tubular, capillary and hollow fiber membranes. Tubular membranes typically may have diameters larger than about 10 mm (millimeters); capillary membranes typically may have diameters between about 0.5 mm and about 10 mm; hollow fiber membranes typically may have diameters less than about 0.5 mm. Tubular membranes may have a functional layer on the inside or lumen side of the membrane and therefore a permeate flow may be from the inside or lumen side to the outside of the membrane. The functional layer of capillary membranes may be either on the inside or outside and therefore the permeate flow may be either from the inside out or from the outside in. The functional layer of hollow fiber membranes may be on the outside and therefore the permeate flow may be from the outside into the inside or lumen side.

Various embodiments may also provide an arrangement for determining at least one pore-related parameter of a porous material, the arrangement including a chamber configured to receive a volatile liquid, the chamber including a support structure, wherein the porous material may be received by the support structure to be arranged spaced apart from and over the volatile liquid, and a mass determination device upon which the chamber may be positioned. The arrangement may include features or structures as described in the context of the arrangement 100.

Various embodiments may also provide an arrangement for determining at least one pore-related parameter of a porous material, the arrangement including a chamber configured to receive a volatile liquid, the chamber including a support structure, wherein the porous material may be received by the support structure to be arranged spaced apart from and over the volatile liquid, a diffusional resistance element to be arranged spaced apart from and over the porous material, wherein the diffusional resistance element may be configured to resist diffusion of vapor of the volatile liquid so as to control evaporation of the volatile liquid, and a mass determination device upon which the chamber may be positioned. The arrangement may include the porous material. The arrangement may include features or structures as described in the context of the arrangement 100.

In various embodiments, for a flat porous material (e.g., 160), a seal structure may be provided to minimise or prevent lateral liquid and vapor loss. In various embodiments, for a tubular porous material (e.g., 160), for example, hollow fibers, the hollow fibers may be sealed at each end and laid horizontally in the chamber or cell (e.g., 102). The hollow fibers need not be arranged at the bottom of the chamber or cell. A seal structure may not be necessary for hollow fiber membranes and/or the seal structure need not contact the hollow fiber membranes.

In various embodiments, the base plate or base portion of the chamber 102 need not have a recess to accept a porous material (e.g., the hollow fibers).

In various embodiments, when evapoporometry is used to characterize hollow fiber membranes, the hollow fiber membranes may be arranged elevated slightly above the base of the chamber or cell (e.g., 102) via an appropriate support (e.g., clamps or a planar structure) (e.g., 104), rather than being placed at the base of the chamber or test cell 102. This may avoid meniscus effects that may be present if the hollow fibers are rested on the bottom of the chamber or cell 102. That is, the wetting liquid may be drawn in by capillary action between the base of the chamber 102 and the bottom of the hollow fiber(s). In other words, placing the hollow fibers at the bottom of the chamber may result in menisci of the volatile liquid (e.g., 150) at the base of each hollow fiber. As the liquid in this meniscus evaporates, it may behave like or similar to evaporation from progressively smaller pores, thereby distorting the pore-size distribution (PSD). Accordingly, such an effect may be avoided by elevating the hollow fibers via an appropriate support structure (e.g., 104).

In various embodiments, when using evapoporometry to determine the pore-size distribution of hollow fibers, it may not be necessary to create a vapor-tight seal between the base of the chamber or test cell (e.g., 102), the upper portion of the chamber or test cell, and the porous material sample (e.g., hollow fibers) (e.g., 160). While a vapor-tight seal may work well for flat sheet membranes for which a good seal may be attained around the perimeter of the membrane, it may not work well for hollow fibers that do not provide a uniform surface on which a good seal may be achieved. As it may not be possible to create a vapor-tight seal at the ends of the hollow fibers, there may be loss of vapor through the two ends of each hollow fiber. Further, in various embodiments, the hollow fibers are not sealed between the base plate and the upper portion of the chamber or test cell.

In various embodiments, the porous material (e.g., 160) need not be saturated with the volatile liquid (e.g., 150) before placing it at the bottom of the test cell. Saturating the porous material prior to putting it in the chamber or test cell (e.g., 102) may cause some loss of volatile liquid owing to evaporation during the transfer process. The porous material (e.g., hollow fibers) may be placed elevated slightly above the bottom of the chamber or test cell and may then be saturated with the wetting liquid by injecting a thin layer of the wetting volatile liquid such that it may cover all the hollow fibers. Capillary action then may draw the wetting liquid into all the pores of the hollow fibers but not into the lumen (interior portion) of the hollow fibers.

Figure 2:
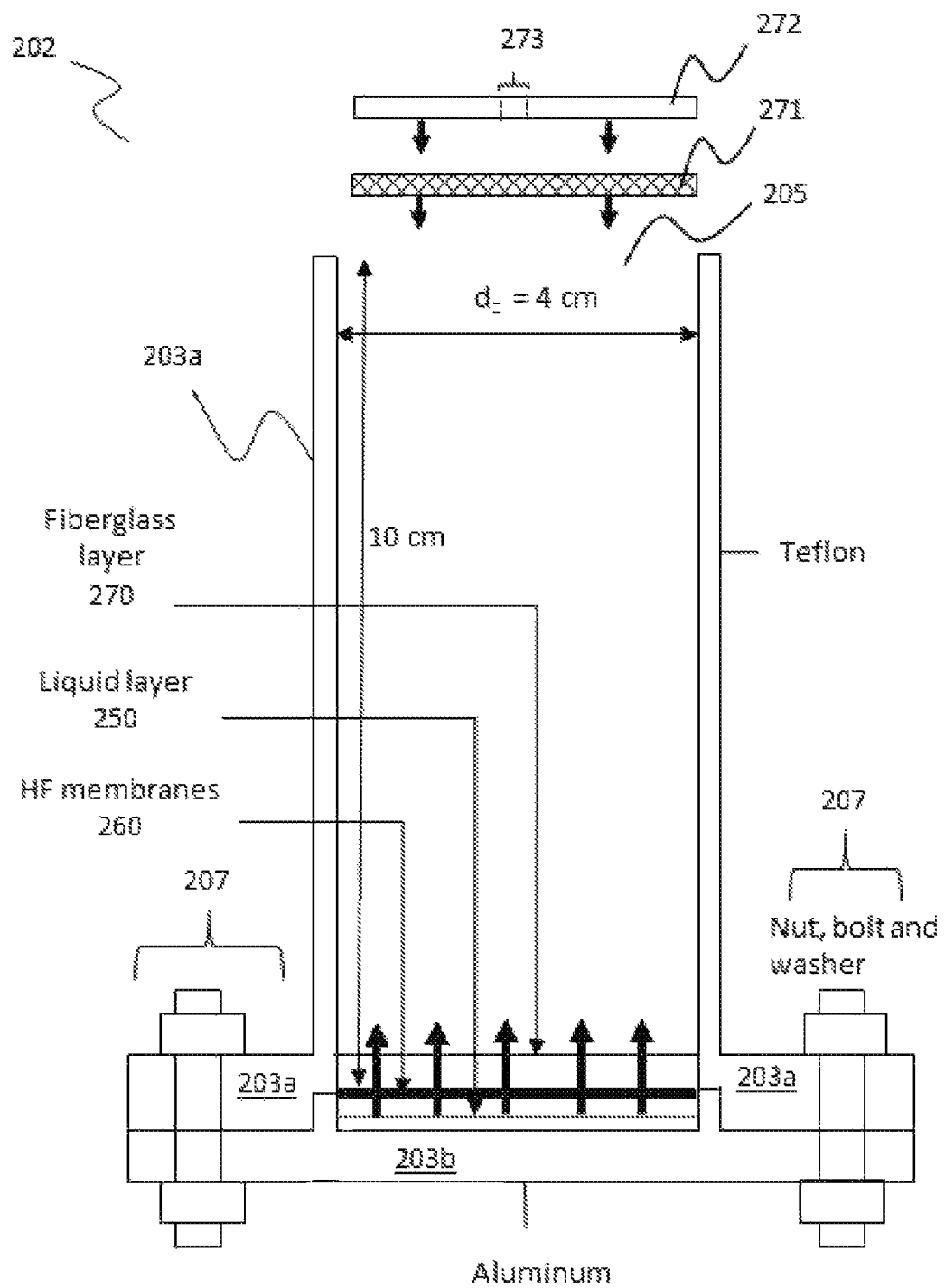
FIG. 2 shows a schematic view of a chamber or test cell for determining at least one pore-related parameter of a porous material, according to various embodiments.

In various embodiments, the mole fraction, $x_{AO}$, as indicated in Equation 4 may be obtained from the evaporation rate in a vertical cylindrical test cell, for example, as shown in FIG. 2 to be described later below.

In various embodiments, the evaporation rate during evapoporometry characterization should be controlled. If the evaporation rate is too slow, the characterization procedure may take an excessively long time. If the evaporation rate is too high, it may compromise the accuracy of the mass determination device (e.g., a microbalance- or other device capable of measuring mass on a microgram scale). Preferably, the mass loss rate during evapoporometry characterization should be less than about $1 \times 10^{-6}$ gmol/s to minimise or avoid compromising the accuracy of the mass determination device. The evaporation rate may be controlled in several ways, three of which will be described herein below, although it should be appreciated that other ways may also be employed.

The evaporation rate may be reduced by inserting a plug of fibrous material such as fiberglass in a chamber or test cell, elevated slightly above the porous material being characterized.

The evaporation rate may also be reduced by employing a covering structure having a small hole (e.g., a vent hole). The covering structure may be arranged within the chamber (or test cell) or may be employed as a cap (or lid) to be removably attached or secured to the top of the chamber. The cap may be attached or secured, for example, by snap-fitting onto the chamber, screwing onto the chamber or by means of clamps. The hole in the covering structure may be sufficiently small to ensure that it is the controlling resistance for the overall mass transfer of vapor out of the chamber or test cell. As non-limiting examples, the size range of the hole in the covering structure that is used to reduce the evaporation rate may vary from as small as approximately 1 mm to a diameter nearly equal to that of the test cell, which, for example, may be from about 4 cm to about 10 cm. The covering structure (e.g., in the form of a cap) may be removable to accommodate another covering structure (e.g., in the form of a cap) having a different hole size or diameter in order to extend the range of evaporation rates that may be controlled in this manner. In various embodiments, the covering structure may include an iris diaphragm so that the hole size or diameter may be varied.

The evaporation rate may also be reduced by employing a microporous membrane or a microporous filter. The microporous membrane or the microporous filter may be arranged within the chamber (or test cell) or may be employed at the top of the chamber. The microporous membrane or the microporous filter may be secured in a rigid holder so that the membrane or the filter in the holder may be positioned reproducibly in the chamber. The microporous membrane or the microporous filter (e.g., with its holder) may be employed as a cap (or lid) at the top of the chamber. Accordingly, a cap or lid that includes or consists of a microporous membrane or a microporous filter may be provided, to be attached or secured to the top of the chamber. The cap may be attached or secured, for example, by snap-fitting onto the chamber, screwing onto the chamber or by means of clamps. The characteristic pore size of the microporous membrane or filter may be chosen to appropriately reduce the evaporation rate. Materials that may be used for the membrane or the filter may include microporous membranes or filters having a pore size in the microfiltration range of about 0.1 micron to about 100 microns that do not interact with the volatile liquids used in evapoporometry characterization; these may include polytetrafluoroethylene (Teflon®), polyethylene, polypropylene, polydimethylsiloxane, polyvinylidene fluoride, poly(ethylene chlorotrifluoroethylene), and others. The microporous membrane or the microporous filter (e.g., in the form of a cap) may be removable to accommodate another cap or lid having a different microporous membrane or the microporous filter (e.g., in the form of a cap) with a different characteristic pore size.

As described above, it should be appreciated that each of the fiberglass, the covering structure, or the microporous membrane (or microporous filter) may act as a diffusional resistance element. In various embodiments, at least one of the fiberglass, the covering structure, or the microporous membrane (or microporous filter) may be employed as the diffusional resistance element. The diffusional resistance element used to reduce the evaporation rate may be placed anywhere in the chamber or test cell provided that it does not touch the porous material or porous sample being characterized. However, it may be advantageous to have the diffusional resistance element, for example, configured as a cap, to be attached or secured to the top of the chamber so that it may be easily removed, for example to insert a different porous sample for characterization or to replace it with another cap having a different hole size or membrane or filter insert.

In various embodiments, the diffusional resistance element (e.g., in the form of a cap or lid) used to reduce the evaporation rate may have a hole or membrane whose effective area may be varied to accommodate different evaporation rates.

In various embodiments, the weight of the diffusional resistance element (e.g., in the form of a cap or lid) should be as small as possible to ensure that the total weight of the chamber or test cell, the porous sample, and the cap may not exceed the tare weight of the mass determination device (e.g., microbalance); a typical 10 microgram resolution microbalance has a tare capacity of approximately 230 grams; a typical 5 microgram resolution microbalance has a tare capacity of approximately 40 grams. Based on the premise that the weight of the cap may be approximately 10% of that of the chamber or test cell, the cap should weigh less than approximately 20 grams when a 10 microgram microbalance is used for EP and should weigh less than 4 grams when a 5 microgram resolution microbalance is used for EP.

In various embodiments, the diffusional resistance element (e.g., in the form of a cap or lid) used to reduce the evaporation rate may have one or more of the following characteristics: (1) the diffusional resistance element has to be the dominant resistance to mass transfer out of the chamber or test cell; (2) the diffusional resistance element may either be removable to permit accommodating different hole sizes or different microporous membrane or filter inserts, or may have an adjustable effective area to permit accommodating different evaporation rates; (3) any material used in or for the diffusional resistance element may be non-interacting with the vapor of the volatile liquid used in the evapoporometry chamber or test cell; (4) any material used in or for the diffusional resistance element may be or should be non-wetting to the volatile liquid used for evapoporometry characterization; or (5) the diffusional resistance element may be sufficiently lightweight so that it does not make the chamber or test cell mass exceed the tare capacity of the mass determination device (e.g., a microbalance or other device capable of measuring mass on a microgram scale).

FIG. 2 shows a schematic view of a chamber or test cell 202 for determining at least one pore-related parameter of a porous material, according to various embodiments. As may be observed in FIG. 2, a pre-saturated porous material (e.g., pre-saturated hollow fiber membranes 260) may be placed into the chamber 202 slightly elevated above the bottom of the chamber 202. A thin layer of volatile liquid (e.g., volatile wetting liquid) 250 may be supplied or added at the bottom of the chamber 202 under the fiber membranes 260, but not touching the fibers 260.

In more detail, the chamber or test cell 202 may include a flanged cylindrical Teflon® chamber or upper portion 203a, open at one end (e.g., the top end 205), with an inside diameter of about 4 cm and a length of about 10 cm. The flanged upper portion 203a may be secured to a flanged aluminium (Al) base or base portion 203b, for example, bolted to the flanged aluminium base portion 203b by means of nuts, bolts and washers, collectively represented by 207.

The chamber 202 may be filled with a known or predetermined amount of a wetting non-interacting liquid or volatile liquid, which may form a thin liquid layer 250 at the bottom or base portion 203b of the chamber 202. The porous material 260 may be placed in the chamber 202 slightly elevated from the volatile liquid 250.

Using a plurality of hollow fiber (HF) membranes as an example for the porous material 260, the fibers of the HF membranes 260 may be sealed (e.g., heat-sealed) at both ends so as to avoid evaporation from the fiber lumen. The hollow fibers 260 may then be saturated, for example, by immersing them in a wetting liquid, which may be similar to the volatile liquid 250, for several hours. Due to the small pore sizes of the HF membranes (e.g., polyvinylidene fluoride (PVDF) and polyacrylonitrile (PAN) membranes) 260 and the use of wetting liquids (e.g., isopropyl alcohol (IPA) or water) as the volatile liquid 250, capillary wicking may cause complete saturation of the pores without any penetration into the lumen of the HFs that would have distorted the pore-size distribution (PSD). Such a design may minimise or prevent any lateral leakage without using O-rings.

The hollow fibers 260 may be laid and clamped, for example, by means of a support structure (not shown), between the upper portion 203a and the base portion 203b of the chamber 202 so that the HF membranes 260 are not in contact with the cell base and the volatile liquid layer 250. The presaturated HFs 260 may be spaced approximately 1 mm apart using two small metal clips and may be placed longitudinally slightly elevated above the bottom of the chamber or test cell 202.

The vapor of the volatile liquid 250 may initially diffuse upward from the evaporating liquid layer 250 and may subsequently diffuse from the surface of the membranes 260 owing to evaporation from the pores of the HF membranes 260. A layer of fiberglass 270 having a thickness of about 1 to 10 cm (e.g., about 1 cm) may be placed approximately 1 mm above the hollow fibers (HFs) 260 to provide a diffusional resistance that may control the rate of mass transfer of the volatile liquid 250, for example when water or isopropyl alcohol (IPA) is used as the volatile liquid 250; this may also ensure uniform supersaturation conditions at the surface of the membranes 260. Therefore, the layer of fiberglass 270 may act as a diffusional resistance element. The layer of fiberglass 270 may be necessary to avoid the rapid evaporation rates that may be associated with free convection when wetting liquids such as water, whose vapor is less dense than air, are used in evapoporometry (EP). Excessively high evaporation rates may cause rapid loss of pore mass (or liquid mass in the pores) and thereby may result in distortion of the pore-size distribution (PSD). They may also cause evaporative cooling that may result in a non-quantifiable reduction in the vapor pressure. Free convection may be damped within the layer of fiberglass 270 that may then create a diffusional resistance in the chamber or test cell 202 that may control the rate of mass transfer. While there may still be free convection in the chamber 202, the mass transfer may be dominated by the dominant diffusional resistance. In other words, a resistance owing to the free convection may be insignificant as compared to the diffusional resistance of the fiberglass 270.

In various embodiments, additional or alternative to the layer of fiberglass 270, a membrane 271 (shown disassembled from the chamber 202 in FIG. 2) may be provided as a diffusional resistance element. The membrane 271 may be arranged in a holder (not shown). The membrane 271 may be removably arranged within the chamber 202, spaced apart from the membranes 260, or the membrane 271 (e.g., with its holder) may be configured as a cap or lid to be removably attached or secured to the top end 205 of the chamber 202. It should be appreciated that different membranes may be provided, for example, membranes of different materials and/or pore sizes, depending on the desired evaporation rate of the volatile liquid 250.

In various embodiments, additional or alternative to the layer of fiberglass 270 and/or the membrane 271, a covering structure 272 (shown disassembled from the chamber 202 in FIG. 2) may be provided as a diffusional resistance element. The covering structure 272 may include a hole (e.g., a vent hole) 273 to allow diffusion of a portion of the vapour of the volatile liquid 250 out of the chamber 202. The covering structure 272 may be removably arranged within the chamber 202, spaced apart from the membranes 260, or the covering structure 272 may be configured as a cap or lid to be removably attached or secured to the top end 205 of the chamber 202. The diameter of the hole 273 of the covering structure 272 may be fixed or may be variable, for example, by means of an iris diaphragm. It should be appreciated that different covering structures may be provided, for example, covering structures having vent holes of different sizes or diameters, depending on the desired evaporation rate of the volatile liquid 250.

For flat sheet membranes, the membranes may be sealed using O-rings between two flanges of a test cell to prevent any lateral vapor leakage from the volatile liquid. In contrast, as described above, the placement and sealing of HFs 260 for EP characterization may be handled differently. Overlying the HFs 260 with a free-standing liquid layer, which may be used in EP characterization of flat sheet membranes which may involve covering the flat sheet membranes with a thin layer of wetting liquid, should be avoided as this may result in residual liquid clinging to the HFs 260 whose subsequent evaporation may distort the PSD. Therefore, for HF membranes 260, a thin layer of wetting liquid 250 may be added at the bottom of the chamber 202 slightly below the HFs 260 so as to avoid the possibility of liquid clinging to the HFs 260. Furthermore, the number and arrangement of the HFs 260 in the chamber 202 that may affect the mass-transfer dynamics may also be determined.

Figure 3:
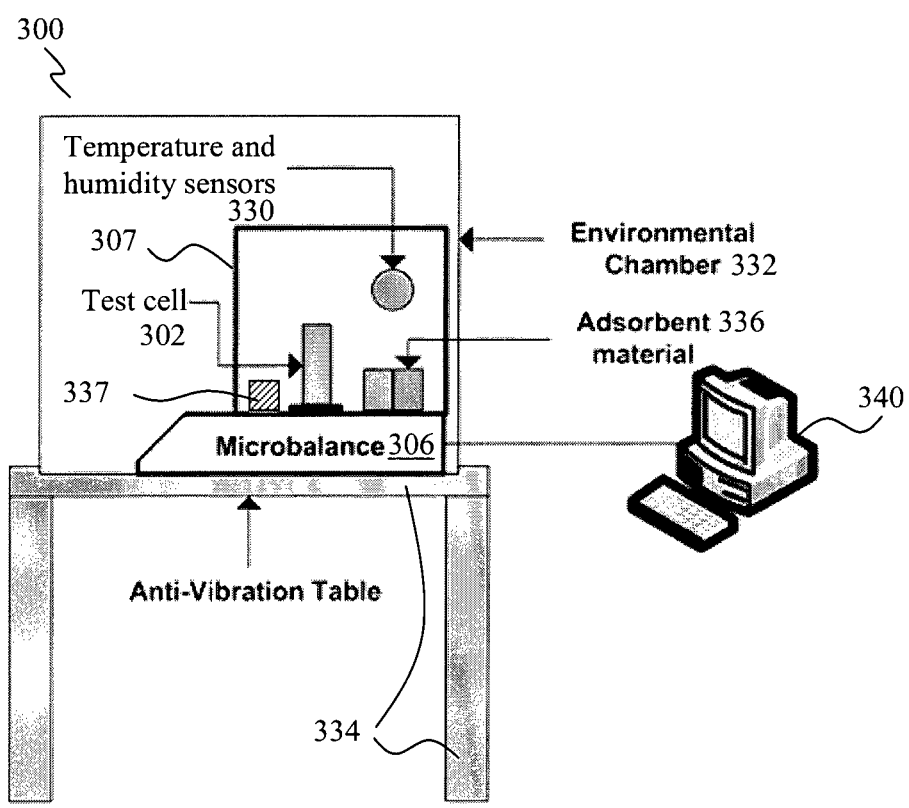
FIG. 3 shows a schematic view of an arrangement for determining at least one pore-related parameter of a porous material, according to various embodiments.

FIG. 3 shows a schematic view of an arrangement 300 for determining at least one pore-related parameter of a porous material, according to various embodiments, illustrating a chamber or test cell being placed in a vibration-isolated microbalance equipped with temperature and humidity sensors. In detail, a chamber or test cell 302, such as for example the chamber 202 (FIG. 2) may be placed on a pan of a microbalance 306 equipped with temperature and humidity sensors 330. The microbalance 306 may include a housing 307 to enclose the test cell 302. The microbalance 306 may be placed in a constant-temperature incubator (or environmental chamber) 332 that may rest on an anti-vibration table (or vibration-isolation table) 334. An adsorbent material 336, for example, a silica gel, may be placed in the microbalance chamber or housing 307 as an absorbent to control the vapor concentration. Vapor of the volatile liquid may initially diffuse upward from the evaporating liquid layer (e.g., 250) and subsequently from the surface of the membranes owing to evaporation from the pores. A static-charge mitigation source (e.g., a Polonium (Po) source) 337 may be positioned within the housing 307 of the microbalance 306 (or other device capable of measuring the mass on the microgram scale). The static-charge mitigation source 337 may mitigate or avoid static charging that may compromise the accuracy of the microbalance 306. The static-charge mitigation source 337 may be necessary when carrying out EP characterization in a non-humid and/or very dry environment. The microbalance 306 may be coupled to a processor (e.g., a computer, PC) 340. SartoCollect software may be used to record the gravimetric data on the processor 340 every 10 seconds during EP characterization.

Non-limiting examples of the materials and the methods for evaporoporometry (EP) will now be described. EP characterization may be performed on hydrophilic PVDF (polyvinylidene fluoride) UF (ultrafiltration) HF (hollow fiber) membranes with a nominal pore diameter of about 35 nm that may include a 0.21 mm layer of hydrophilic PVDF on a polyethylene terephthalate mesh support. EP characterization may also be performed on hydrophilic polyacrylonitrile (PAN) UF HF membranes whose thickness may be about 0.5 mm; no information is available for the pore diameter. The membrane porosity may be determined by saturating the HF membrane with isopropyl alcohol (IPA), quickly wiping any excess IPA from the surface, and then weighing it. After evaporating the IPA by placing the membrane in a vacuum oven at about 50° C. for about 4 hours, it may be weighed again. The membrane porosity then may be determined from the difference between the wet and dry weights and the mass density of IPA. The porosity of the PVDF layer removed from the support layer may be about 65%. The porosity of the PAN HF membrane may be about 60%. These porosities may be used in determining the onset of liquid loss owing to evaporation from the pores. For the EP measurements, 12 PVDF or 18 PAN HF membranes may be heat-sealed at both ends and presaturated by immersing them in the wetting liquid overnight.

Milli-Q™ water and isopropyl alcohol (IPA) may be used as the volatile wetting liquids.

Figure 4A:
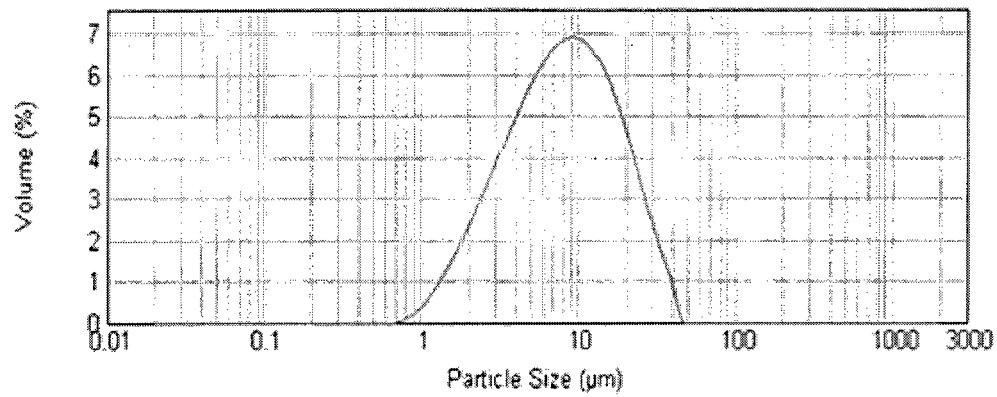
FIGS. 4A and 4B show plots of the particle-size distributions for the foulants: bentonite and humic acid, respectively.
Figure 4B:
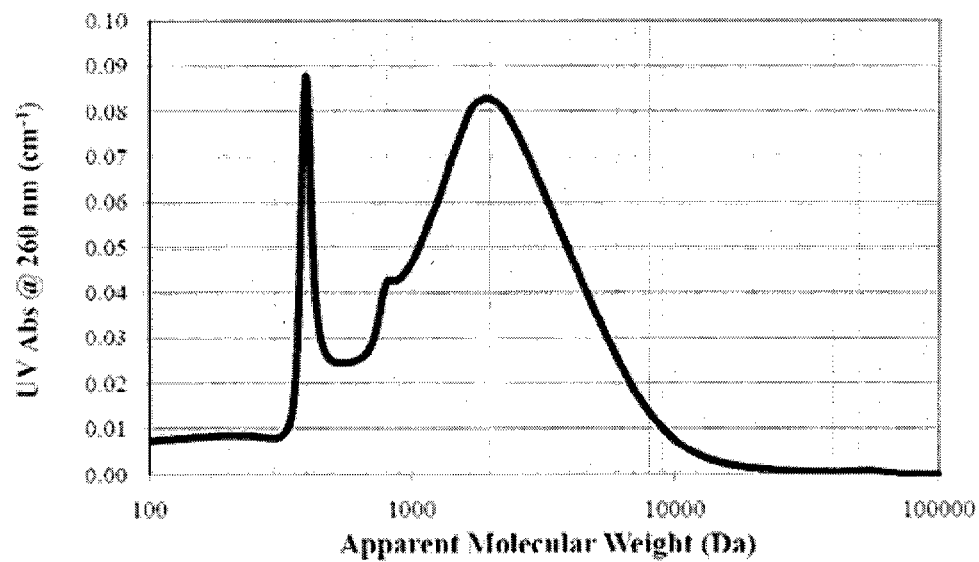

For determination of the effect of internal pore fouling on the pore-size distribution (PSD), a mixture of analytical grade bentonite and humic acid may be used, where bentonite may serve to form a cake layer that may be easily removed via backwashing and aeration, whereas humic acid may also cause internal pore fouling. The particle-size distribution of the bentonite may be determined via laser light-scattering and the results may be as shown in FIG. 4A. As may be observed, the particle diameter may range from about 0.7 μm to about 50 μm with an average of about 8.1 μm. The particle-size distribution of the aggregated humic acid may be determined via high pressure size exclusion chromatography (HPSEC) and the results may be as shown in FIG. 4B. As may be observed, the molecular weight may range from about 300 Da to about 10000 Da, which is within the range that may be concentrated by UF membranes.

The determination of internal pore fouling on the PSD of the PVDF membranes may be done using a bench-scale dead-end filtration apparatus with a bundle of seven HFs having a length of about 15 cm that may be immersed in a tank with an aqueous feed mixture of about 1.0 g/l of bentonite and about 20 mg/l of humic acid. A flux of about 70 l/m² h may be used with periodic backwashing and aeration for 9 cycles that may involve about 15 minutes of filtration followed by about 2 minutes of backwashing at the same flux, with no backwashing done after the 9$^{th}$ cycle. The amount of permeate withdrawn may be controlled by a peristaltic pump that may provide suction on the permeate side.

A capillary flow porometer may be used for LDP determination of the PSD of the HF membranes. Galwick™, a perfluoropolyester-based non-volatile wetting liquid, whose surface tension is about 15.9 mN/m, may be used with this porometer.

Data analysis and the related procedure will now be described.

The evaporation rate of a liquid layer (e.g., a free-standing liquid layer) may be used to determine the overall mass-transfer coefficient $k_x$, as provided below:

$$k_x = -\frac{4W_A^\circ}{\pi d_c^2 \ln(1 - x_{A0}^\circ)}, \quad \text{(Equation 8)}$$

where $W_A^\circ$ is the evaporation rate of the free-standing liquid layer, $d_c$ is the diameter of the chamber or test cell (e.g., 202, FIG. 2), and $x_{A0}^\circ$ is the value of $x_{A0}$ at normal saturation conditions (e.g., above a flat interface between the liquid and the vapor).

Since $k_x$ is a constant at a fixed temperature and pressure, the same value may apply for mass transfer in the chamber or test cell during evaporation from the pores (or during pore draining). Hence, the instantaneous value of $x_{A0}$ may be determined from $W_A$, the progressively decreasing evaporation rate during evaporation from the pores (or during pore draining), from the following:

$$x_{A0} = 1 - \exp\left(-\frac{4W_A}{\pi d_c^2 k_x}\right), \quad \text{(Equation 9)}$$

Figure 5A:
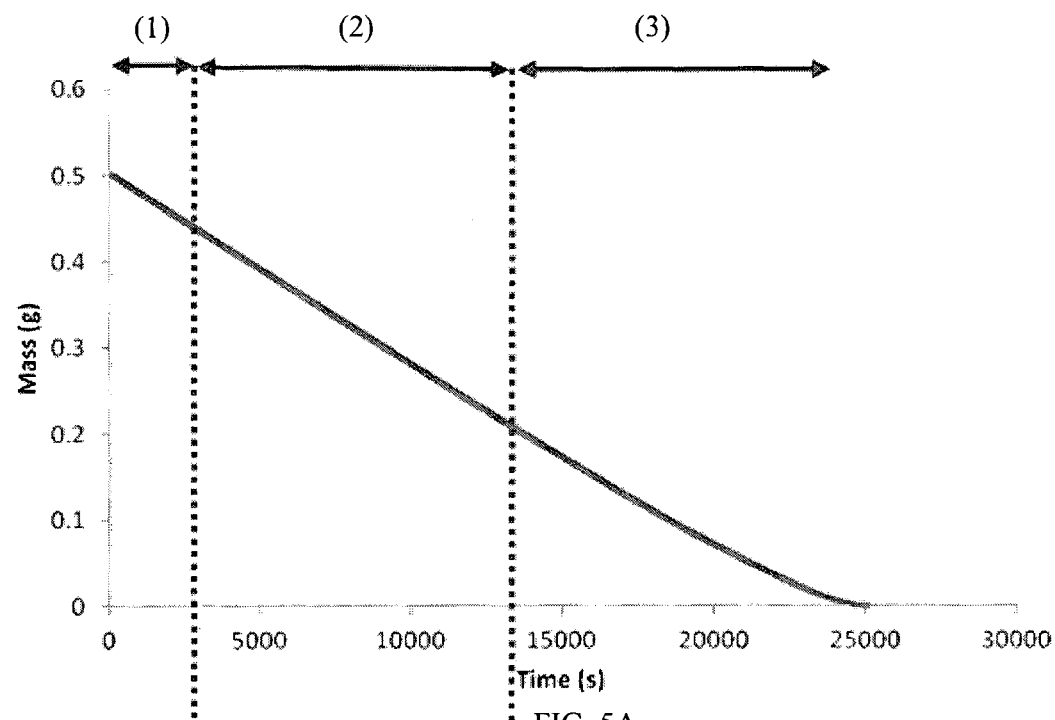
FIGS. 5A and 5B show plots of the mass as a function of time and the evaporation rate as a function of time, respectively, for evapoporometry (EP) characterization.
Figure 5B:
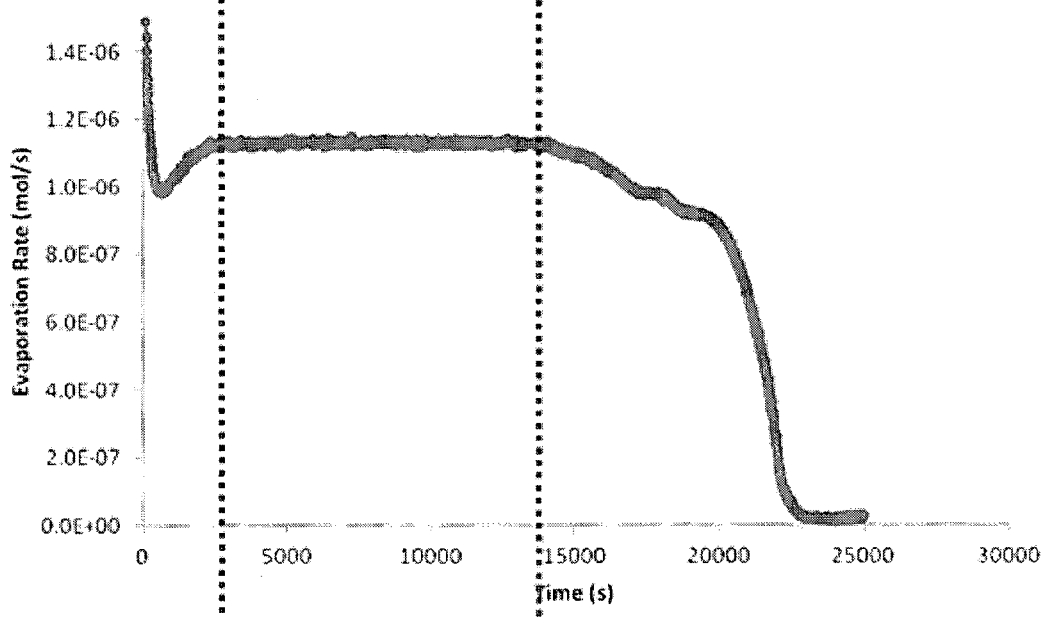

FIGS. 5A and 5B show plots of the mass as a function of time and the evaporation rate as a function of time, respectively, for evapoporometry (EP) characterization, illustrating representative raw data for EP characterization. Three stages may be evident in FIGS. 5A and 5B, indicated as stages 1, 2 and 3. Stage 1 represents the transient period, stage 2 represents the free-standing liquid evaporation and stage 3 represents the pore-liquid evaporation.

Referring to FIG. 5A, initially during the first stage (stage 1), the microbalance (e.g., 306, FIG. 3), the chamber or test cell (e.g., 202, 302), and the evaporating volatile liquid (e.g., 250) may come to a steady-state temperature established by the environmental chamber (e.g., 332). After the steady-state temperature is reached, the free-standing liquid evaporation period may commence during which the mass may decrease linearly as a function of time (stage 2), thereby implying a constant evaporation rate. Once this free-standing liquid layer has evaporated, evaporation from the pores may begin (or in other words, the pore-draining period may begin) (stage 3). It is assumed that evaporation from the membrane pores may not occur until the free-standing liquid (e.g., 250) has evaporated due to the vapor-pressure depression by the pores.

Representative data for the instantaneous evaporation rate ($W_A$) may be as shown in FIG. 5B. After a transient period (stage 1) during which steady-state is being established, $W_A$ may become constant corresponding to evaporation from the free-standing liquid layer (stage 2). After the liquid layer has evaporated, $W_A$ may decrease owing to evaporation from progressively smaller pores (stage 3).

Pore draining (or evaporation from the pores) may be expected to occur when the measured value of $W_A$ deviates from the experimentally determined value $W_A^\circ$ by more than three standard deviations from the mean. However, if the porosity of the membranes being characterized may be known (for example, by being measured), the inception of pore draining may be determined based on the amount of residual mass in the saturated (or pre-saturated) membrane. In other words, pore-draining or evaporation from the pores may be assumed to begin when the amount (e.g., mass) of residual liquid in the test cell is equal to the mass of the liquid in the presaturated HF membranes, e.g., equal to the mass of the liquid in the pores of the fully saturated membranes.

During the stage in which evaporation is occurring from the pores (meaning the pore-draining stage), the decrease of the mass as a function of time may no longer be linear. The evaporation rate may progressively decrease as a function of time. This reduced evaporation rate may be associated with evaporation from pores having progressively smaller diameters.

The instantaneous evaporation rate may be used to determine the mole fraction at the surface of the membrane that may be associated with the vapor-pressure depression caused by the pores from which evaporation is occurring at that instant of time; meaning $x_{A0}$ in Equation 9. In other words, for example, the evaporation rate versus time data during the pore-draining period may be used to determine the mole fraction ($x_{A0}$) associated with the curved interface between the volatile liquid within the pores that are draining at that instant of time and the ambient gas phase. From these values of $x_{A0}^\circ$ and $x_{A0}$, the instantaneous pore diameter may be determined from Equation 4.

The procedure for data analysis will now be described by way of the following non-limiting examples.

The hollow fiber membranes (e.g., 260) may be initially heat-sealed at both ends and presaturated by immersing them in the wetting liquid overnight. The presaturated membranes (e.g., 260) may be arranged with two small metal clips and placed towards the bottom of the chamber or test cell (e.g., 202, 302). The metal clips may help to maintain the presaturated membranes slightly elevated from the bottom of the chamber. A thin layer of wetting liquid (approximately 0.5 ml) (e.g., 250) may be added to the bottom of the chamber or cell (e.g., 202, 302). A layer of fiberglass (e.g., 270) having a thickness of about 1 cm to about 10 cm may be placed approximately 1 mm above the hollow fibers. Sufficient adsorbent material (e.g., 336) may be placed in the housing or chamber (e.g., 307) of a microbalance (e.g., 306). The test cell may be placed on the pan of the microbalance that may be positioned in an environmental chamber (e.g., 332) whose temperature may be maintained at least substantially constant. Mass data may be recorded and stored on a computer or PC every 10 seconds.

Further, replicate measurement on different samples taken from the same batch of membranes may be done rather than re-measurement on the same membrane sample because the dried membranes may be fragile and difficult to handle. Moreover, re-measurement may not be possible for the membranes used in the fouling studies owing to residual deposits in the pores. The following stepwise procedure may be used for the EP data analysis and for each replicate determination of the PSD:

1. Record the instantaneous mass, barometric pressure and temperature every 10 seconds.
2. Determine the instantaneous evaporation rate, $W_A$, from the slope through seven consecutive mass versus time points (data points) and assign this value to the time at the midpoint (e.g., for the first seven data taken from 0 to 60 s, the slope may be assigned to 30 s; for the next seven data extending from 10 to 70 s, it may be assigned to 40 s, etc.). It should be appreciated that any odd number of consecutive mass versus time points (data points) may be employed, including but not limited to one, three, five, seven, nine or any higher number. In various embodiments, seven data points may be optimal.

3. Plot the values of $W_A$ versus time, for example, as shown in FIG. 5B.
4. Determine the vapor pressure of the volatile liquid at the temperature recorded. This may mean that the vapor pressure in atmospheres of the volatile liquid at the temperature recorded may be determined.
5. Determine the theoretical mole fraction at the surface of the wetting liquid layer, $x_{A0}$, by dividing the vapor pressure by the recorded barometric pressure.
6. Determine the mean value and the standard deviation (SD) of $W_A$ during the time period when it is 'constant' in order to obtain $W_A^\circ$, the evaporation rate of the free-standing liquid layer. These estimates of the evaporation rate of the free-standing liquid layer $W_A^\circ$ and the SD may be used to assess whether the data set may be reliable. The SD should be less than about 0.5% of the mean for an acceptable data set.
7. Plot the mass versus time for the region in which $W_A$ is essentially or at least substantially constant. Put a trend line through the mass versus time data to determine the evaporation rate for the free-standing liquid layer; this slope divided by the molecular weight of the wetting liquid is the experimental value of $W_A^\circ$. This method for determining $W_A^\circ$ may be more accurate than any type of averaging of the instantaneous value of $W_A$, including for example, the averaging method used in step 6 above.
8. Determine the mass-transfer coefficient, $k_x$, from the values of $W_A^\circ$ and $x_{A0}^\circ$ using Equation 8.
9. Determine when evaporation from the pores (or pore draining) begins. If the porosity of the membranes being characterized is known, the inception of evaporation from the pores (or pore draining) may be determined based on the amount of residual mass in the saturated membrane, e.g., when the instantaneous mass of liquid may be equal to that in the presaturated membranes. If the porosity is not known, evaporation from the pores (or pore draining) may be assumed to occur when the measured value of $W_A$ deviates from the experimentally determined value of $W_A^\circ$ by more than three standard deviations from the mean.
10. Determine the instantaneous mole fraction of the wetting liquid at the surface of the membranes, $x_{A0}$, for the pore diameter or size that is draining or at which evaporation is occurring using the instantaneous values of $W_A$ and $k_x$ and Equation 9.
11. Determine the diameter of the pores that are draining or from which evaporation is occurring at any point (or any instant) in time from the values of $x_{A0}$, $x_{A0}^\circ$ and the temperature using Equation 4.
12. Determine the average pore diameter between consecutive sets of two pore diameters and record the resulting value (or in other words the resulting average pore diameter).
13. Determine the mass associated with each average pore diameter from the difference in the instantaneous mass associated with the two pore diameters used in determining the particular average pore diameter.
14. Sort the resulting pore diameters into bins having a width of about 5 nm (e.g., the 20 nm bin may contain all the pores having diameters between about 17.5 nm and about 22.5 nm).
15. Sum the masses of all the pores in each bin and set this equal to the mass of that bin.
16. Plot the pore-size distribution (PSD) as the percent of the total pore mass in each bin as a function of the pore diameter.
17. Determine the mass-average pore diameter via numerical integration using the pore-size distribution (PSD) (e.g., for the data shown in FIG. 7A, $d_{avg}$=18.5 nm for Run 1 and $d_{avg}$=14.0 nm for Run 2, and for the data shown in FIG. 8A, $d_{avg}$=35.0 nm for Run 1 and $d_{avg}$=34.1 nm for Run 2).

Results and determination of the pore-size distribution (PSD) of polyacrylonitrile (PAN) and polyvinylidene fluoride (PVDF) hollow fiber (HF) membranes will now be described. As non-limiting examples, water or isopropyl alcohol (IPA) may be used as the wetting liquid. The contact angle of water on the membranes may not be zero, while the contact angle of IPA on both membranes may be zero due to its lower surface tension compared to the critical surface tension of PAN and PVDF. The static contact angles of water on the PVDF and PAN HF membranes may be about 37.6±1.9 and about 42.2±0.6, respectively, based on three replicate measurements.

Figure 6A:
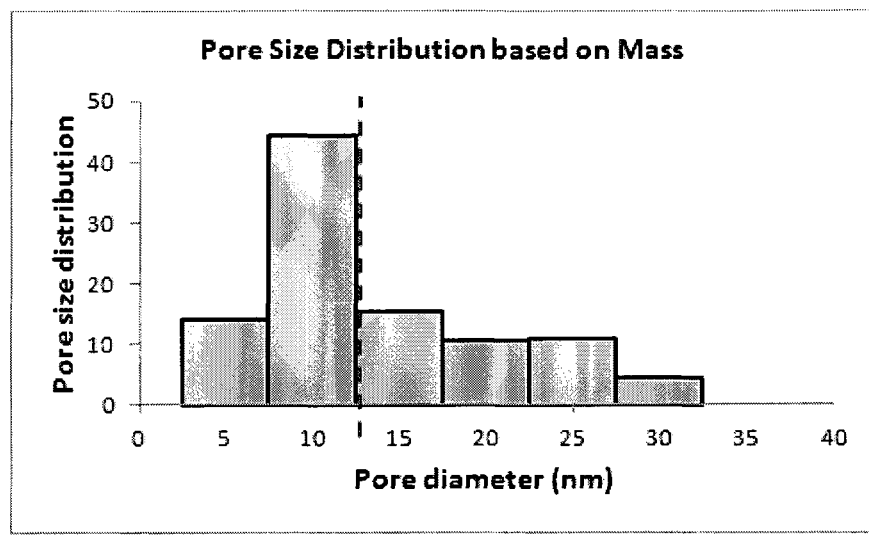
FIGS. 6A and 6B show the respective results of the pore-size distribution (PSD) of a polyacrylonitrile (PAN) hollow fiber membrane determined by evapoporometry (EP) using isopropyl alcohol (IPA) as the wetting liquid, and liquid displacement porometry (LDP).

FIG. 6A shows the results of the pore-size distribution (PSD) of a hollow fiber membrane (e.g., a commercial polyacrylonitrile (PAN) hydrophilic membrane with 1 mm OD (outer diameter) and 0.5 mm ID (inner diameter)) determined by evapoporometry (EP) using isopropyl alcohol (IPA) as the volatile wetting liquid, based on three replicate measurements. The PSD is plotted as a percentage of the total mass (or volume) of the wetting liquid in the pores as a function of the pore diameter, d, in nm. In FIG. 6A, the 5 nm bin includes only pores with diameters from 4-7.5 nm owing to the lower limit of the classical Kelvin equation. The mass-average pore diameter for the PSD from the three replicate measurements as shown in FIG. 6A is about 12.5 nm ($d_{avg}$=12.5±1.1 nm).

Figure 6B:
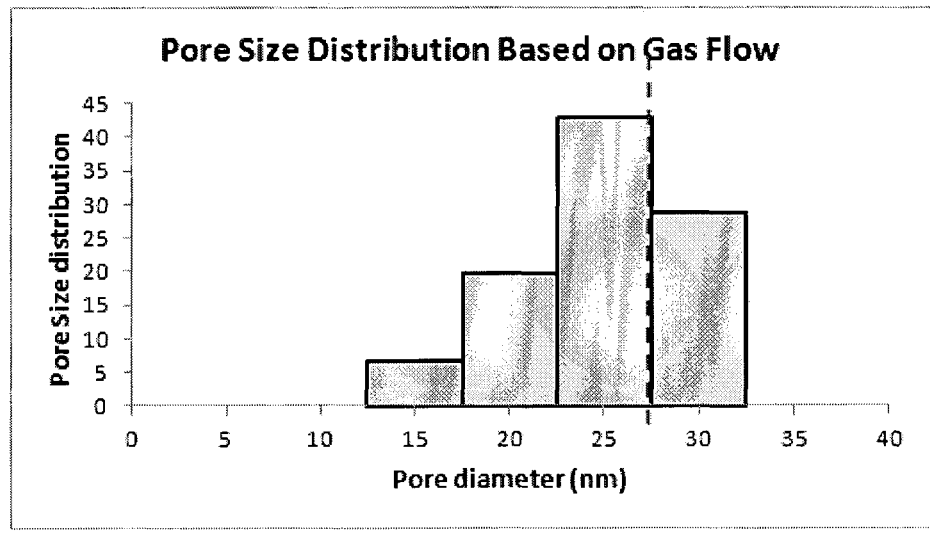

Results of the LDP characterization of the same hollow fiber are as shown in FIG. 6B. The flow-average pore diameter from LDP for three replicate measurements as shown in FIG. 6B is about 27.2 nm ($d_{avg}$=27.2±1.5 nm). LDP cannot detect pores smaller than 14 nm. Moreover, the high applied pressure in LDP also causes compression of the membranes that causes the PSD to be shifted towards smaller pore diameters. In contrast, the EP method may detect pores larger than about 4 nm. This will result in a more realistic average pore diameter for EP measurements.

Figure 7A:
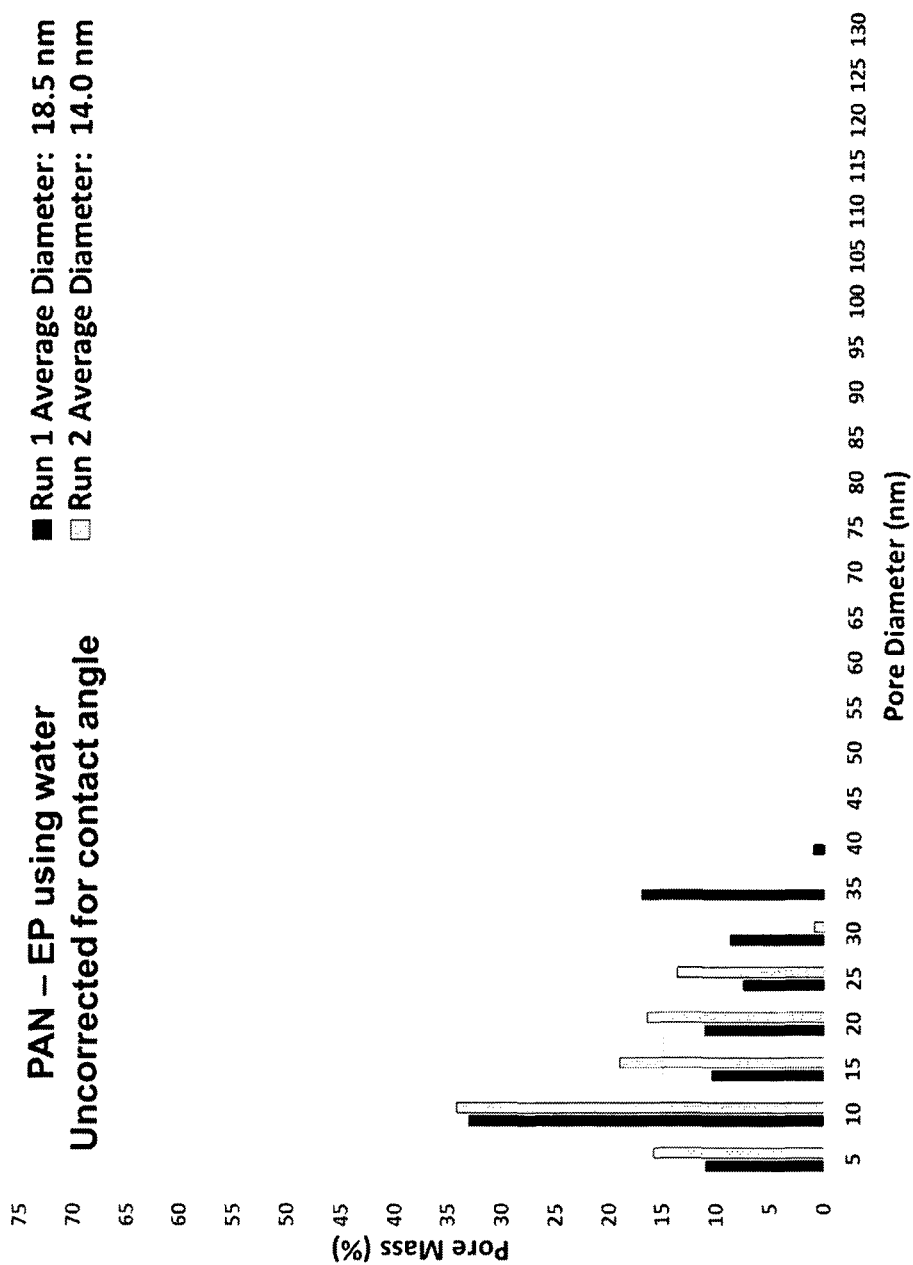
FIGS. 7A and 7B show the results of two replicate runs showing the pore-size distribution (PSD) for polyacrylonitrile (PAN) hollow fiber membranes determined using evapoporometry (EP) with water as the volatile wetting liquid.
Figure 7B:
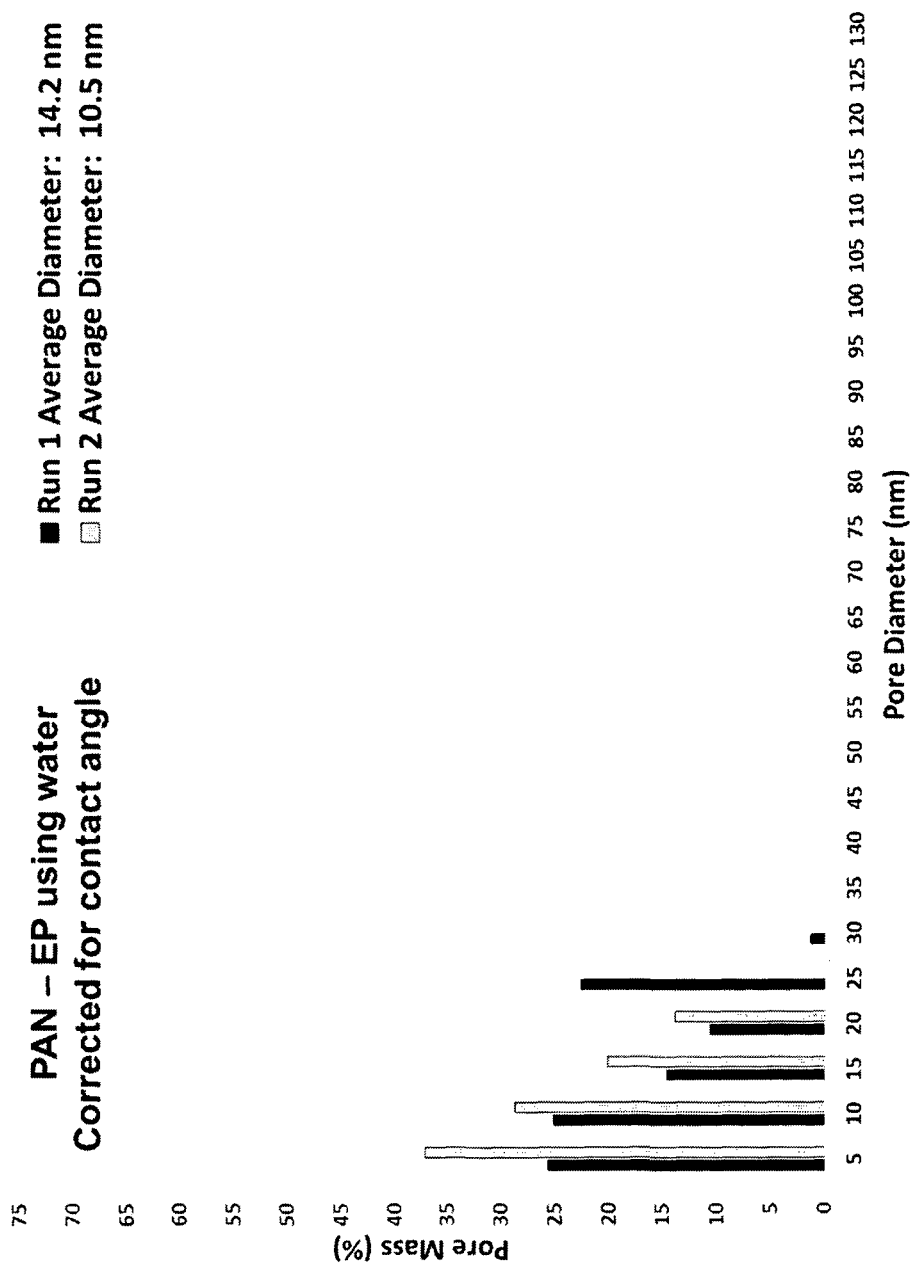

FIGS. 7A and 7B show the results of the pore-size distribution (PSD) determined by evapoporometry (EP) for polyacrylonitrile (PAN) hollow fiber membranes (e.g., commercial polyacrylonitrile (PAN) hydrophilic hollow fiber membranes) using water as the volatile wetting liquid. Two replicate PSDs are shown. The PSD is plotted as a percentage of the total pore mass as a function of the pore diameter, d, in nm. The 5 nm bin includes only pores with diameters from 4 to 7.5 nm owing to the lower limit of the classical Kelvin equation. FIG. 7A shows the PSD determined assuming that the contact angle of water on PAN is zero. FIG. 7B shows the pore-size distribution corrected for the non-zero contact angle of water on PAN, which has been determined to be about 42.2±0.6.

Figure 7C:
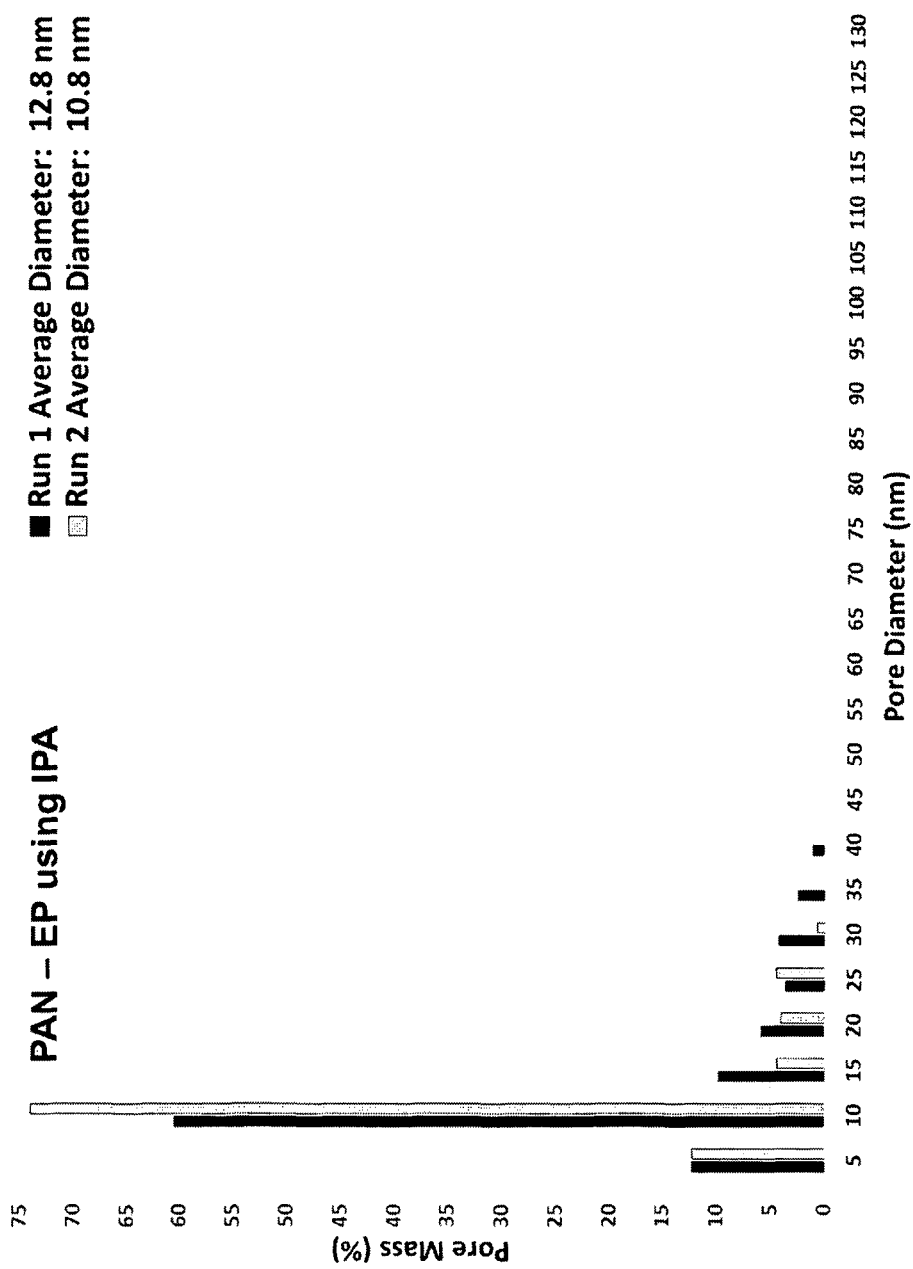
FIG. 7C shows the results of two replicate runs showing the pore-size distribution (PSD) for polyacrylonitrile (PAN) hollow fiber membranes determined using evapoporometry (EP) with isopropyl alcohol (IPA) as the volatile wetting liquid.
Figure 7D:
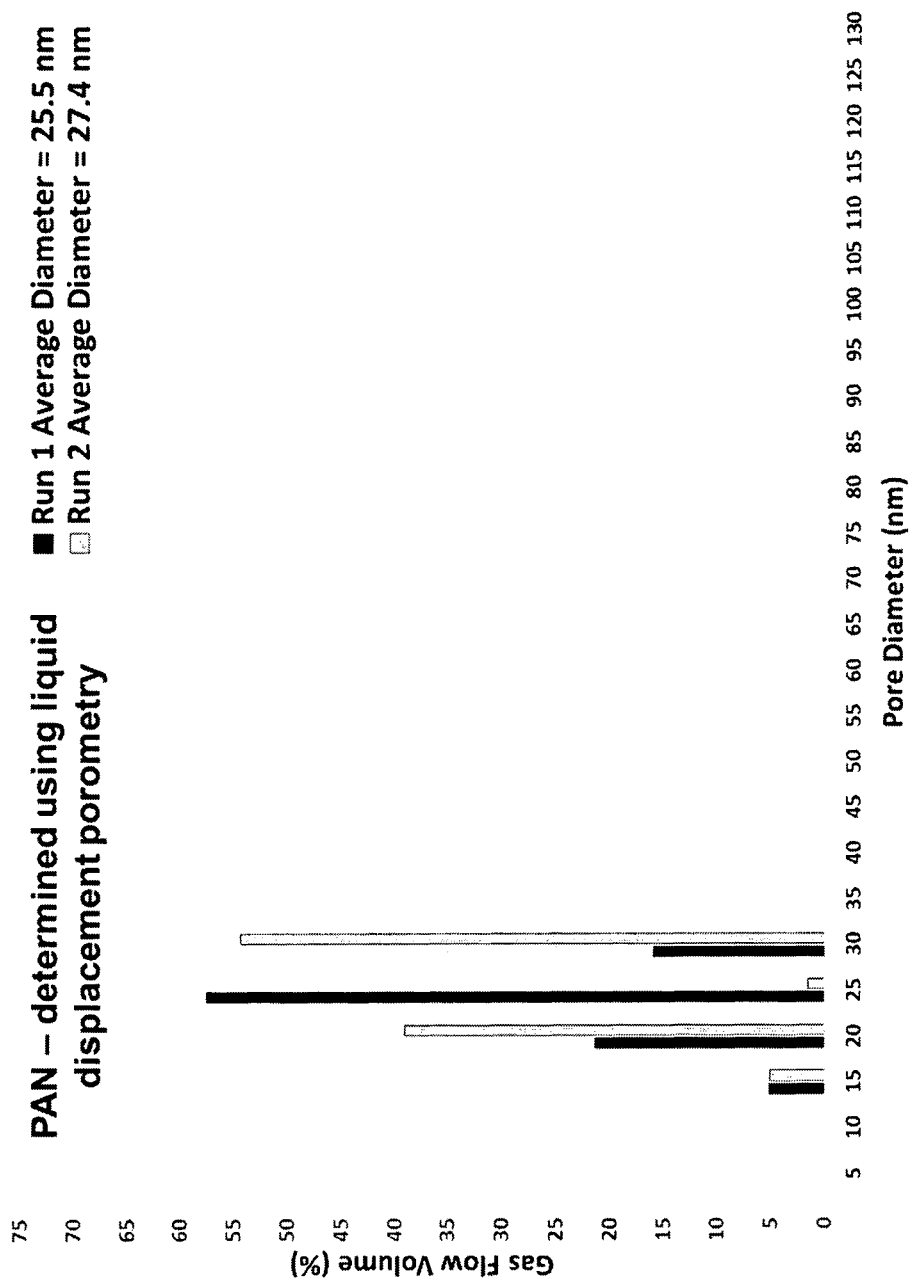
FIG. 7D shows the results of two replicate runs showing the pore-size distribution (PSD) for polyacrylonitrile (PAN) hollow fiber membranes determined using liquid displacement porometry (LDP).

FIG. 7C shows the PSD determined by evapoporometry (EP) for polyacrylonitrile (PAN) hollow fiber membranes using isopropyl alcohol (IPA) as the volatile wetting liquid for which the contact angle may be identically zero. FIG. 7D shows the PSD determined via liquid displacement porometry (LDP) for the PAN membrane (e.g., a commercial PAN hydrophilic hollow fiber membrane) with Galwick™ as the nonvolatile wetting liquid, for which the vertical axis is based on the percentage of the gas flow.

The horizontal scale is the same in FIGS. 7A to 7D to allow comparison of the respective PSDs. The mass-average pore diameters for the PAN HF membranes based on the PSD determined by EP using water corrected for the nonzero contact angle and IPA are about 12.4±1.9 nm and about 11.8±1.0 nm, respectively. The replicate measurements agree well for both water and IPA; moreover, the PSD and the mass-average pore diameter determined using water agree well with those determined using IPA. The flow-averaged pore diameter determined from LDP for two replicates in FIG. 7D is about 26.5±1 nm, which is considerably larger than the values determined via EP using both water and IPA. One reason for this is that LDP could not detect pores smaller than 14 nm due to the maximum pressure limitations of the instrument; excluding these small pores would cause the flow-average pore diameter to be larger than the EP results. Another reason is that the mass-average diameter determined by EP is based on $d^2$ whereas the flow-average diameter determined by LDP is based on $d^4$; the latter will be larger than the former. In contrast, the EP method employing the classical Kelvin equation may accurately determine the diameter of pores as small as about 4 nm. This may result in a more realistic average pore diameter for EP measurements. It should be appreciated that the vapor-pressure depression effect described by the classical Kelvin equation may be operative for pore sizes considerably smaller than about 4 nm. The evapoporometry (EP) technique described herein may be extended to pore sizes smaller than about 4 nm by appropriate modifications to the classical Kelvin equation.

Figure 8A:
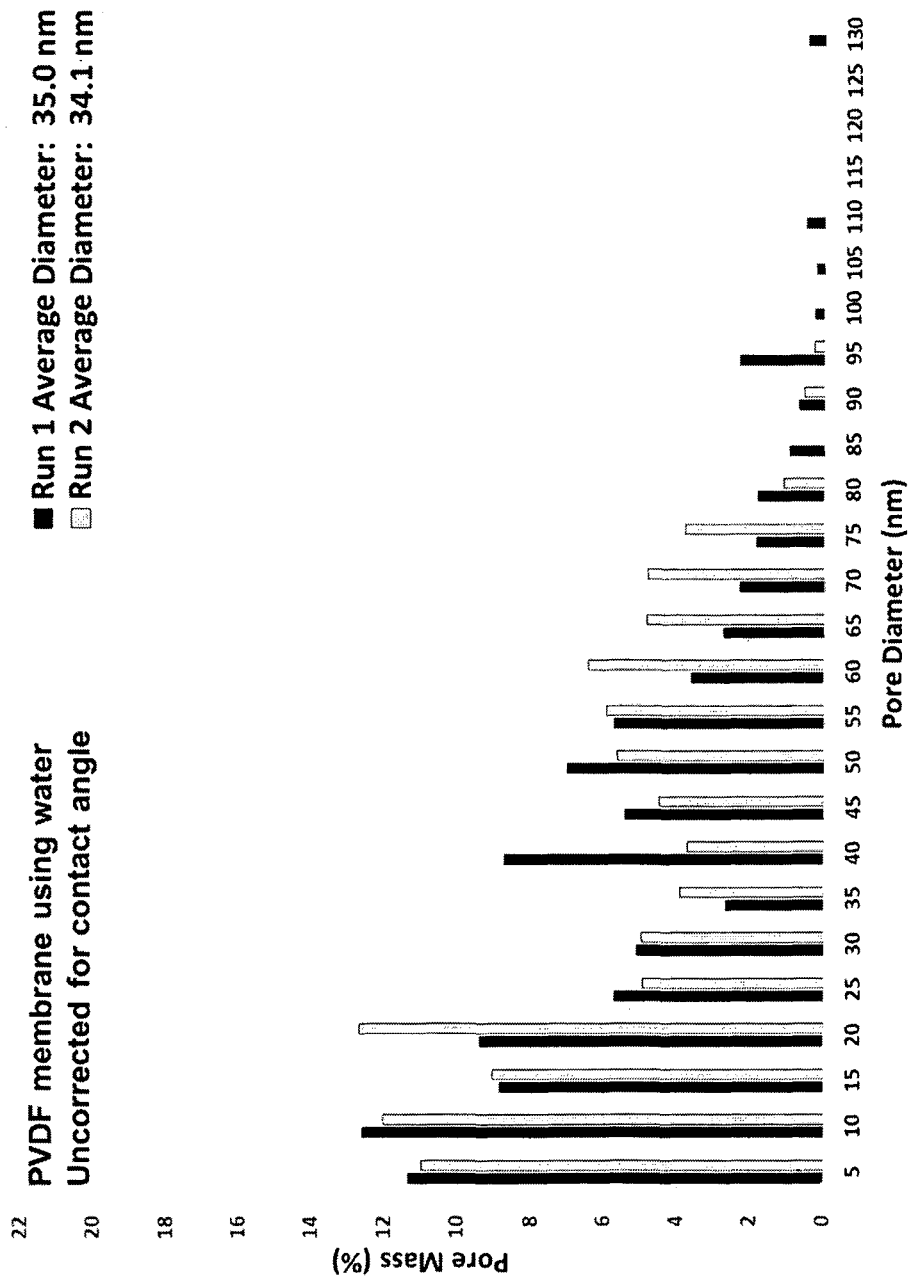
FIGS. 8A and 8B show the results of two replicate runs showing the pore-size distribution (PSD) of a polyvinylidene fluoride (PVDF) hollow fiber membrane determined by evapoporometry (EP) using water as the wetting liquid.
Figure 8B:
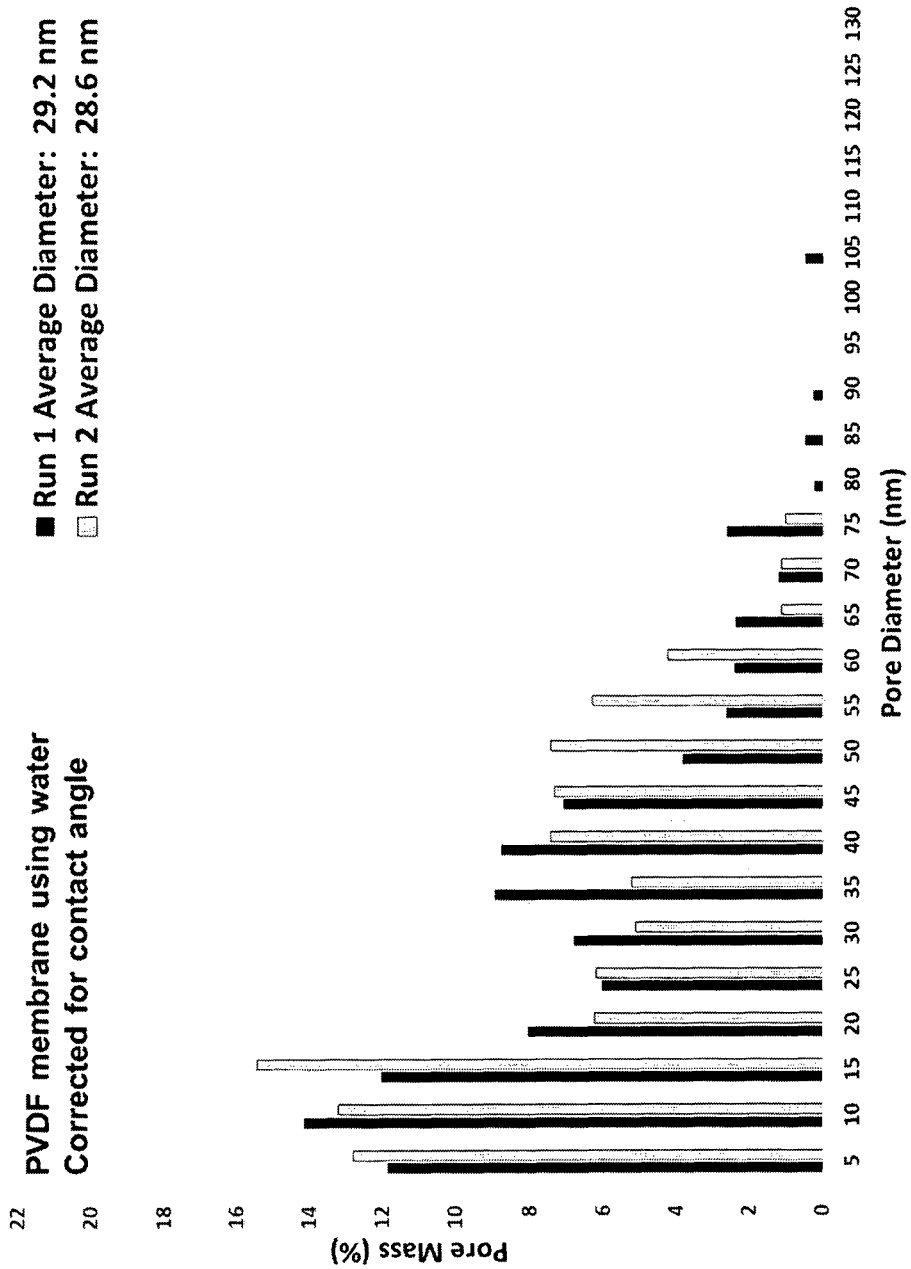

FIGS. 8A and 8B show the results of the pore-size distribution (PSD) determined by evapoporometry (EP) for polyvinylidene fluoride (PVDF) hollow fiber membranes (e.g., commercial polyvinylidene fluoride (PVDF) hydrophilic hollow fiber membranes) using water as the volatile wetting liquid. Two replicate PSDs are shown. The PSD is plotted as a percentage of the total pore mass as a function of the pore diameter, d, in nm. The 5 nm bin includes only pores with diameters from 4 to 7.5 nm owing to the lower limit of the classical Kelvin equation. FIG. 8A shows the PSD determined assuming that the contact angle of water on PVDF is zero. FIG. 8B shows the pore-size distribution corrected for the non-zero contact angle of water on PVDF, which has been determined to be about 37.6±1.9.

Figure 8C:
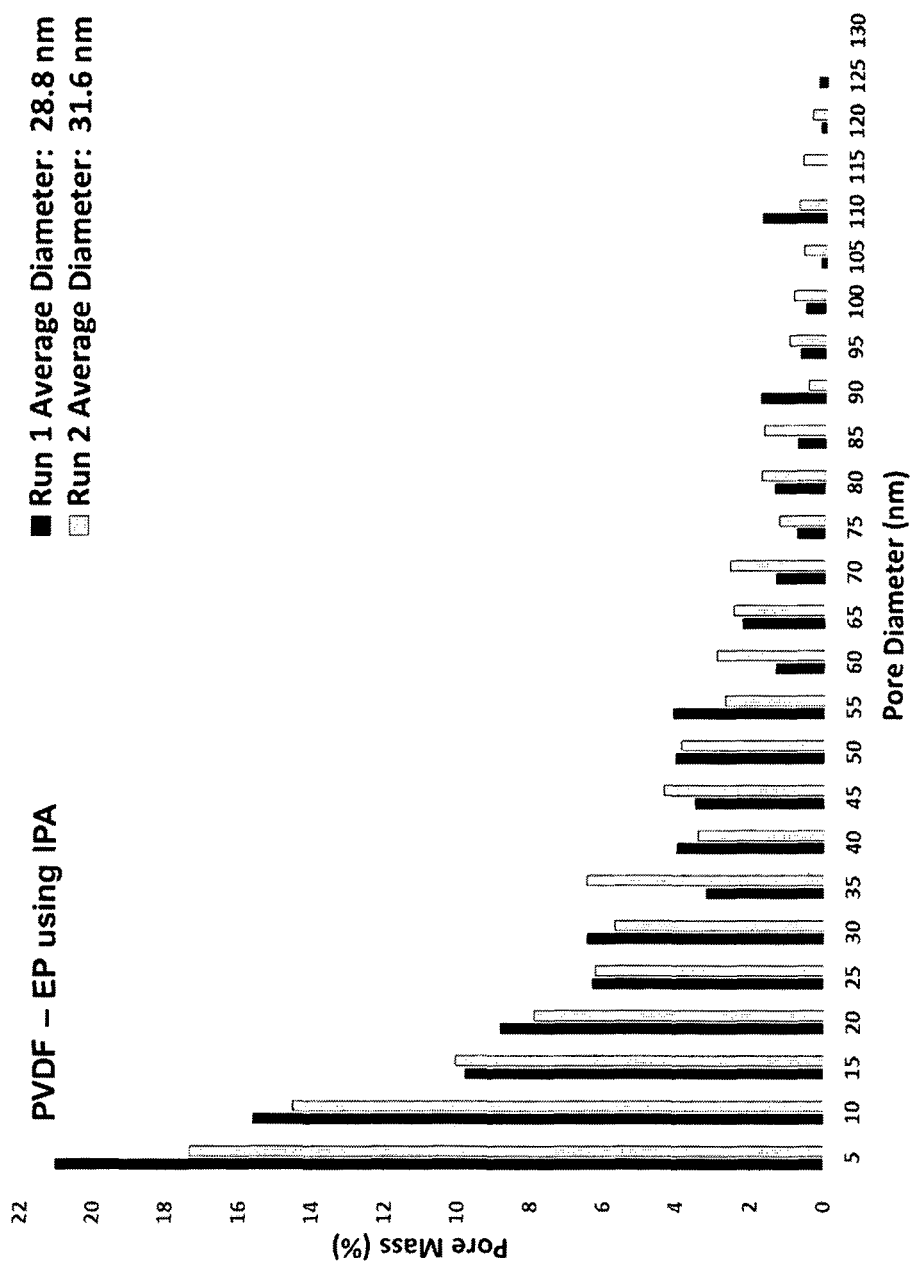
FIG. 8C shows the results of two replicate runs showing the pore-size distribution (PSD) for polyvinylidene fluoride (PVDF) hollow fiber membranes determined using evapoporometry (EP) with isopropyl alcohol (IPA) as the volatile wetting liquid.
Figure 8D:
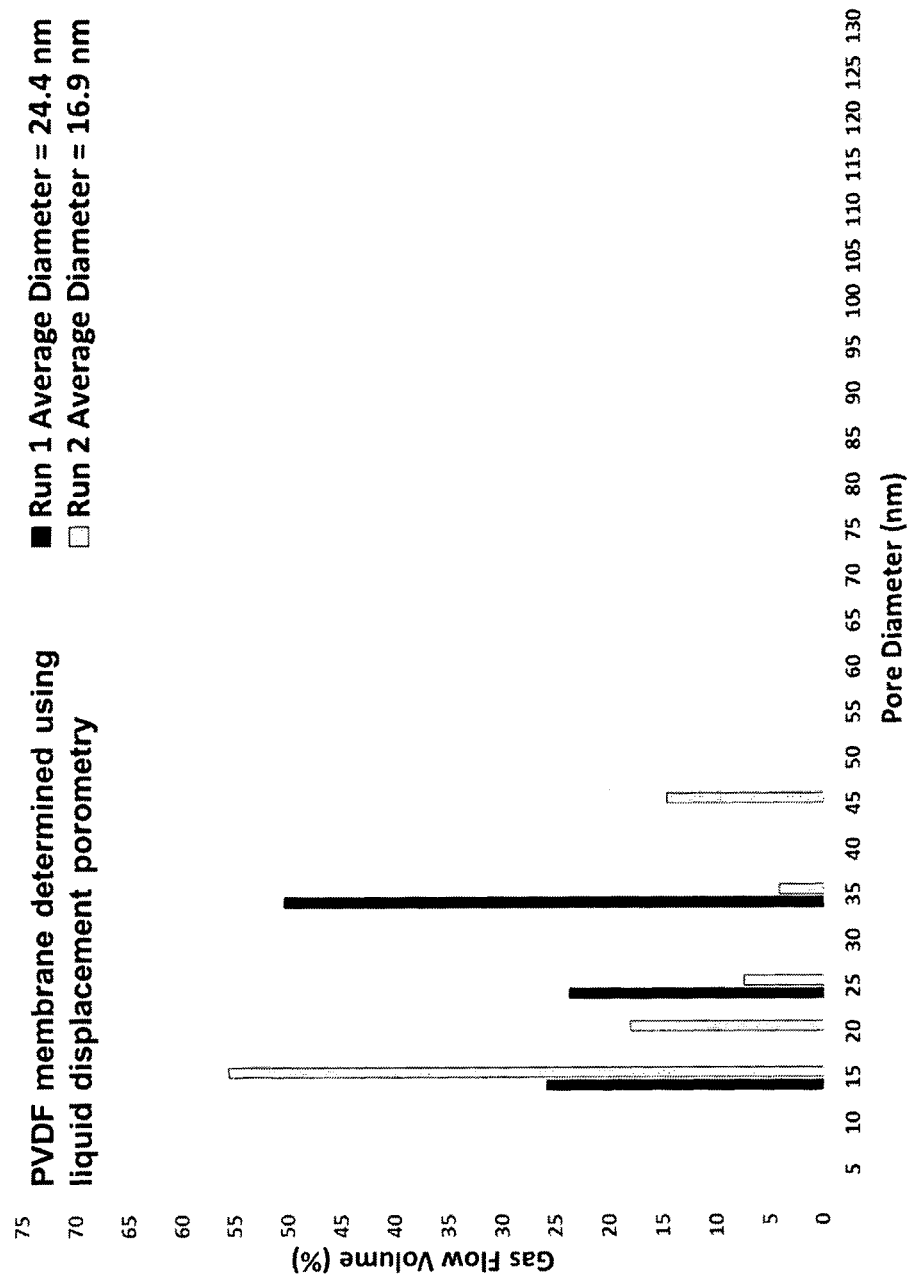
FIG. 8D shows the results of two replicate runs showing the pore-size distribution (PSD) for polyvinylidene fluoride (PVDF) hollow fiber membranes determined using liquid displacement porometry (LDP).

FIG. 8C shows the PSD determined by evapoporometry (EP) for polyvinylidene fluoride (PVDF) hollow fiber membranes using isopropyl alcohol (IPA) as the volatile wetting liquid for which the contact angle may be identically zero. FIG. 8D shows the PSD determined via liquid displacement porometry (LDP) for the PVDF membrane (e.g., a commercial PVDF hydrophilic hollow fiber membrane) with Galwick™ as the nonvolatile wetting liquid, for which the vertical axis is based on the percentage of the gas flow. The mass-average pore diameters for the PVDF HF membranes based on the PSD determined by EP using water corrected for the nonzero contact angle and IPA are about 28.9±0.3 nm and about 29.7±0.9 nm, respectively.

The replicate measurements agree well for both water and IPA for evapoporometry (EP). Moreover, the PSD and the mass-average pore diameter determined using water agree well with those determined using IPA. The average pore diameter is also in reasonable agreement with the nominal pore diameter of 35 nm provided by the manufacturer. The nominal pore diameter supplied by the manufacturer is probably determined by a size-exclusion method, which may be based on determining the pore size for which 90% of a standard particle size is excluded from passing through the membrane. As such, it provides a different metric; moreover, it is not based on a determination of the pore-size distribution.

The flow-averaged pore diameter determined from LDP for two replicates in FIG. 8D is about 20.7±3.8 nm, which is somewhat smaller than the values determined via EP using both water and IPA. This is in marked contrast to the comparison between EP and LDP for the PAN membranes as described above. This disparity is probably due to compaction of the PVDF membrane under the high pressure used in LDP. For example, LDP requires pressures exceeding 6 MPa to displace the low surface tension Galwick™ wetting liquid from a pore with a diameter of 10 nm. In contrast to the PVDF membrane, membrane compaction has not caused the average pore diameter determined by LDP to be smaller for the PAN membrane. A possible explanation lies in the structure of the PAN and PVDF membranes. Whereas the PAN membrane is an integral membrane, the PVDF membrane includes or consists of a thin functional PVDF layer on a support. Quite possibly this marked difference in the structure of the two HF membranes may make the PAN membrane more resistant to compaction.

Table 1 summarizes the average pore diameters determined by EP and LDP for the PVDF and PAN HF membranes. In summary, the average pore diameter determined by EP agrees reasonably well with the nominal pore diameter of 35 nm given by the manufacturer for the PVDF membrane. LDP provides a smaller pore diameter than EP for the PVDF membrane, possibly due to membrane compaction at the high pressures required to characterize the smallest pores. However, LDP provides a larger pore diameter for the PAN membrane possibly because it cannot measure pores smaller than 14 nm and it determines the flow-average rather than the mass-average pore diameter, both of which would shift the average pore diameter towards larger values.

TABLE 1

Average pore diameters determined by evapoporometry (EP) and liquid displacement porometry (LDP) for polyvinylidene fluoride (PVDF) and polyacrylonitrile (PAN) hollow fiber membranes; correction is included for non-zero contact angle of water.

| PSD Method | Nominal 35 nm PVDF [a]uncorrected for contact angle [b]corrected for contact angle | Commercial PAN [a]uncorrected for contact angle [b]corrected for contact angle |
|---|---|---|
| Evapoporometry using IPA | 30.2 ± 1.4 nm | 11.8 ± 1.0 nm |
| Evapoporometry using water | [a]34.6 ± 0.5 nm [b]28.9 ± 0.3 nm | [a]16.3 ± 23 nm [b]12.1 ± 2.8 nm |
| Liquid displacement porometry | 20.7 ± 3.8 nm | 26.5 ± 1.0 nm |

Whereas both water and IPA have been used in the EP characterization of the PAN and PVDF membranes, it may be preferable to use IPA rather than water as the volatile wetting liquid for EP characterization. IPA is far more wetting than water on most membranes due to its lower surface tension. Moreover, IPA may result in far less membrane swelling than water because of its much lower dielectric constant. However, owing to the widespread use of UF membranes for applications involving water, it may be useful to carry out EP characterization of the PSD using both IPA and water in order to assess possible changes in the membrane performance in the actual environment that it may be used.

The change in the pore-size distribution (PSD) of hollow fiber membranes due to internal pore fouling may be investigated by evapoporometry. Use of evapoporometry (EP) for assessing the effect of internal pore fouling on the pore-size distribution (PSD) will now be described by way of the following non-limiting examples.

Measurements may be carried out to evaluate the use of EP for characterizing internal pore fouling in HF membranes. Sufficiently small foulants may enter the membrane pores and may deposit on the pore walls, which may cause partial pore blocking. Also, the number of active pores may be decreased by pore blocking. EP and LDP may be used to evaluate the changes in the PSD of PVDF as well as other HF membranes owing to these effects of fouling.

In order to determine the effect of internal pore fouling on the PSD of nominal 35 nm PVDF HFs, dead-end filtration with a feed including or consisting of about 1 g/l bentonite and about 20 mg/l humic acid may be performed at a filtration flux of about 70 l/m$^2$ h (which may be at least substantially constant). This may involve cycling or periodic backwashing accompanied by aeration with about 15 minutes of filtration followed by about 2 minutes of backwashing with aeration rate at about 0.0011 m/s. The bentonite particles may be too large to cause any internal pore fouling; however, the aggregated humic acid may deposit both in the cake layer on the membrane and within its pores (e.g., see PSDs shown in FIGS. 4A and 4B).

Figure 9:
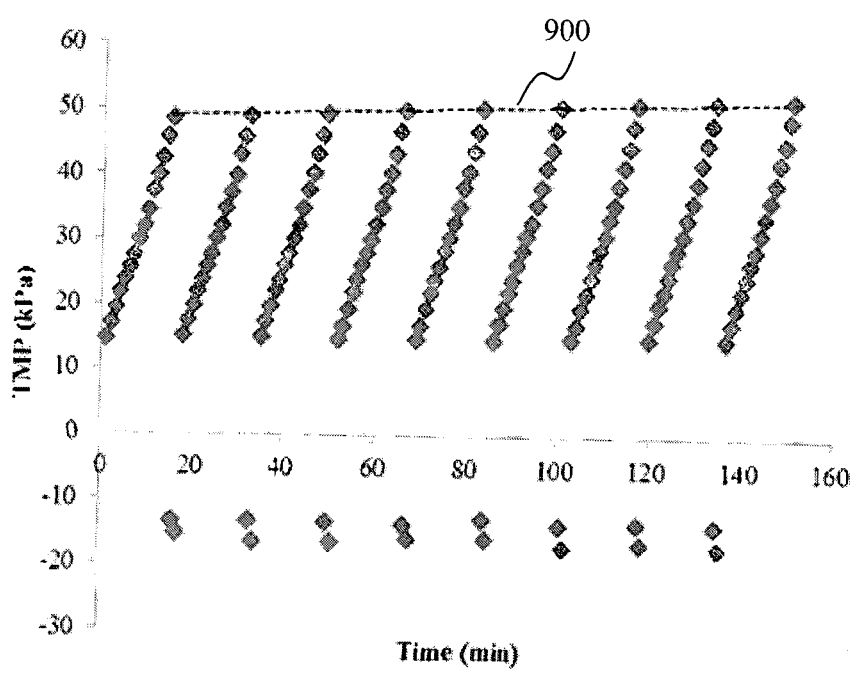
FIG. 9 shows a plot of the transmembrane pressure versus time for dead-end filtration.

FIG. 9 shows a plot of the transmembrane pressure versus time for dead-end filtration for 9 filtration and backwashing cycles. Filtration at a constant flux may cause the TMP to monotonically increase owing to the constant deposition of foulants; backwashing then may cause the TMP to become negative during which time nearly all the foulants may be removed. However, FIG. 9 clearly shows a progressive increase in the maximum TMP with each cycle, which is shown by the dashed line 900. This may be attributed to a gradual increase in the internal pore fouling that may not be totally removed by backwashing.

Figure 10A:
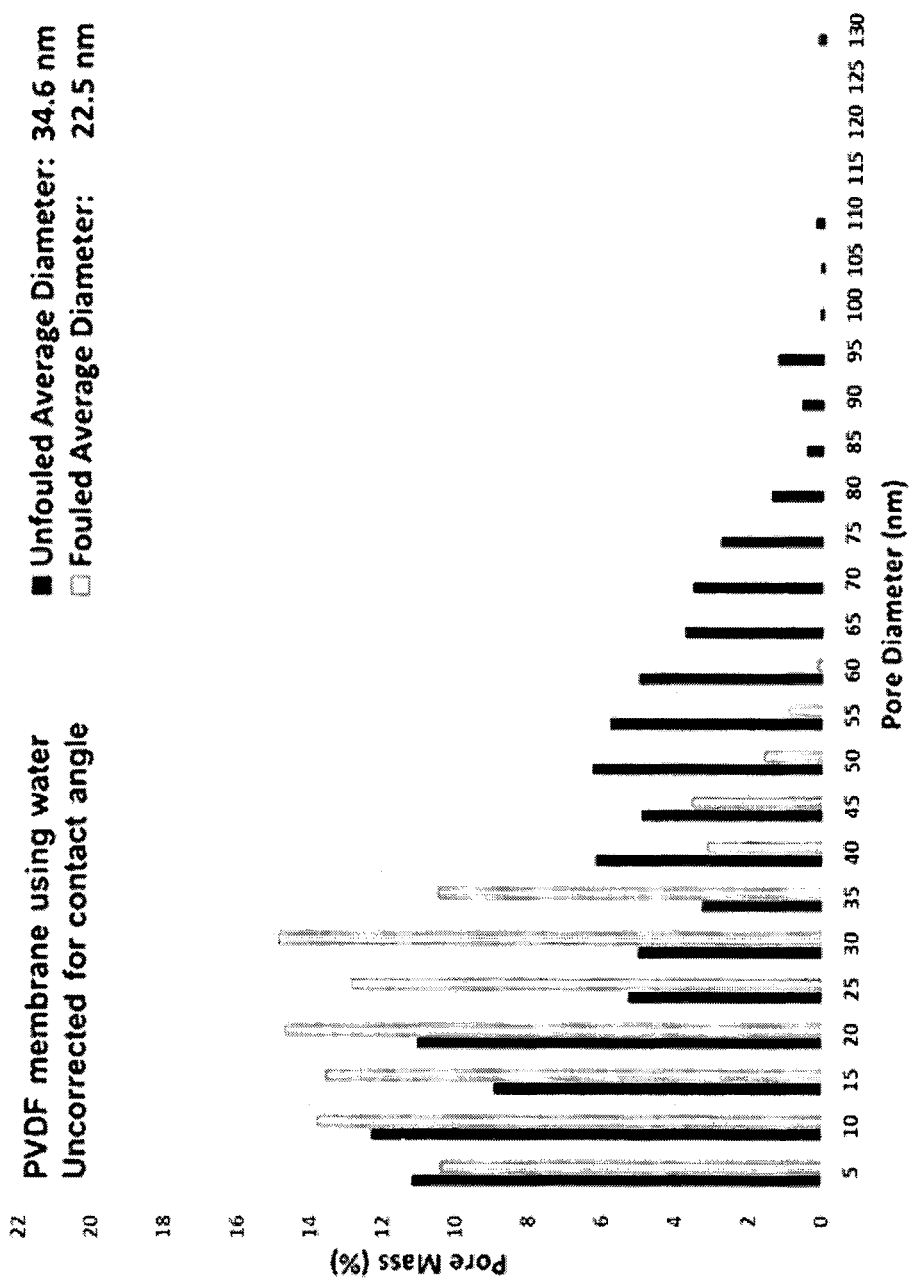
FIGS. 10A and 10B show the results of the pore-size distribution (PSD) determined by evapoporometry (EP) for polyvinylidene fluoride (PVDF) hollow fibers before and after being fouled with foulants.
Figure 10B:
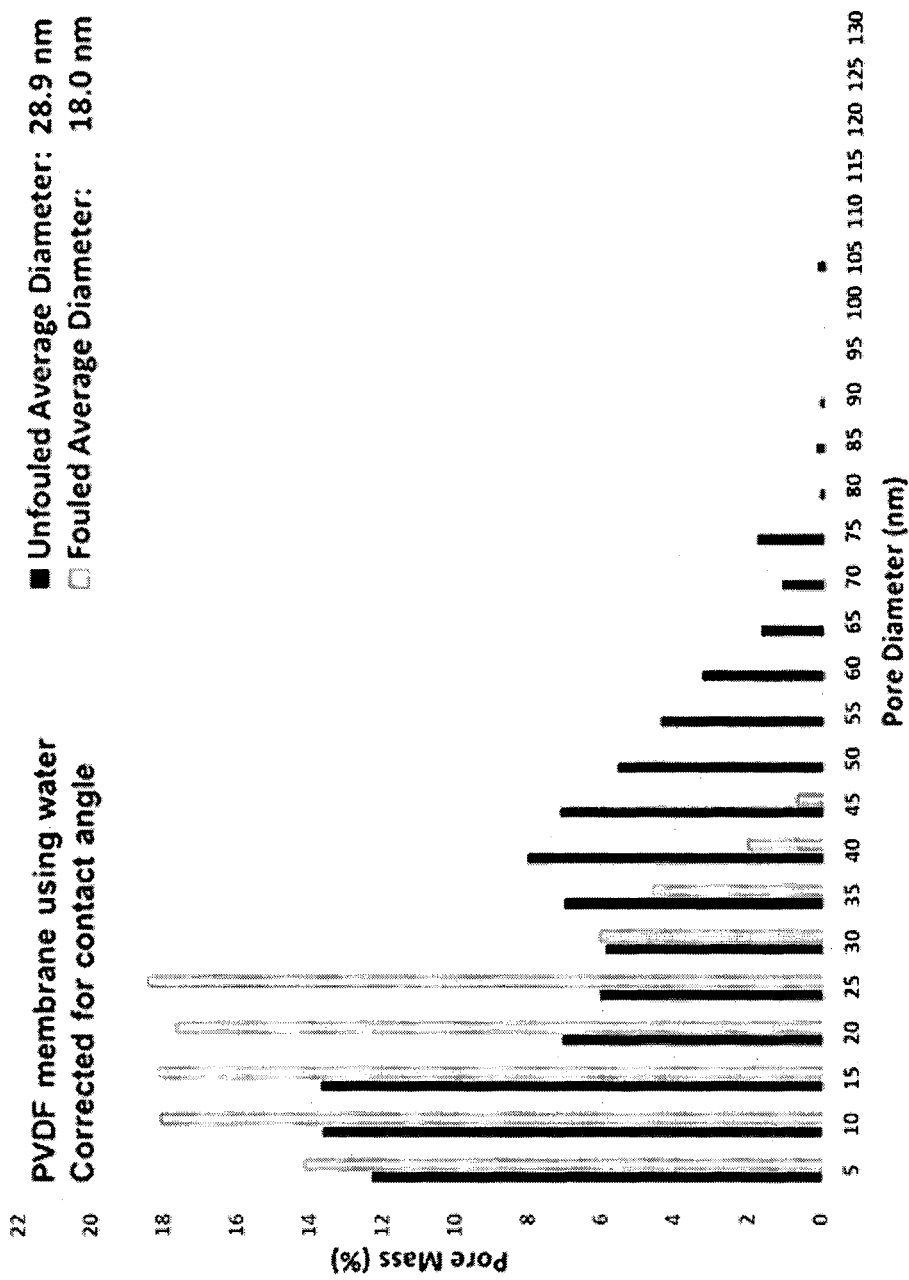

FIGS. 10A and 10B show the results of the pore-size distribution (PSD) determined by evapoporometry (EP) for polyvinylidene fluoride (PVDF) hollow fibers (e.g., PVDF commercial hollow fibers) before and after being fouled with foulants (e.g., a mixture of bentonite particles and humic acid) after 9 cycles of filtration and backwashing. The feed solutions used are Milli-Q™ water for non-fouling determination and an aqueous mixture of about 1.0 g/l of bentonite and about 20 mg/l of humic acid for fouling determination using dead-end filtration at a constant flux of about 70 l/m$^2$ h. No backwashing has been carried out at the end of the 9$^{th}$ filtration cycle after which the cake layer may be removed by rinsing the fibers with water. The fibers may be dried and heat-sealed before the EP characterization.

FIG. 10A shows the results for the PSD determined for the fouled PVDF hollow fiber membranes using water uncorrected for the nonzero contact angle of water on PVDF. As may be observed in FIG. 10A, all the pores with a diameter greater than about 60 nm have disappeared and the pore-size distribution (PSD) may shift towards smaller effective pore diameters due to blockage by the fouling deposits within the pores. The mass-average pore diameter of the fouled membranes in FIG. 10A is about 22.5±1.2 nm compared to about 34.6±0.5 nm for the unfouled membrane. This shift in the PSD may presumably be due to blockage of the pores by foulants. However, interestingly there is not a significant difference between the total mass of water in the pores of the clean and fouled membranes. This may suggest that the fouling may partially block the entrance of some pores on the feed side without any significant penetration into these pores; that is, since evaporation from the pores during EP characterization is determined by the effective diameter at the entrance of the pore, the mass in the unfouled lower reaches of these pores may be attributed to smaller diameters than the actual diameter of the unfouled pores. The large difference in the average pore size may be because of more severe partial pore blocking in the larger pores that may more easily accommodate the aggregated humic acid. FIG. 10B shows the results taking into consideration the non-zero contact angle of water on the PVDF HF membrane which has been determined to be about 37.7±1.9 and permitted correcting the results for the non-zero contact angle of water on the PVDF HF membrane. The mass-average pore diameter of the fouled membranes in FIG. 10B is about 18.0±1.2 nm compared to about 28.9±0.3 nm for the unfouled membrane.

Figure 10C:
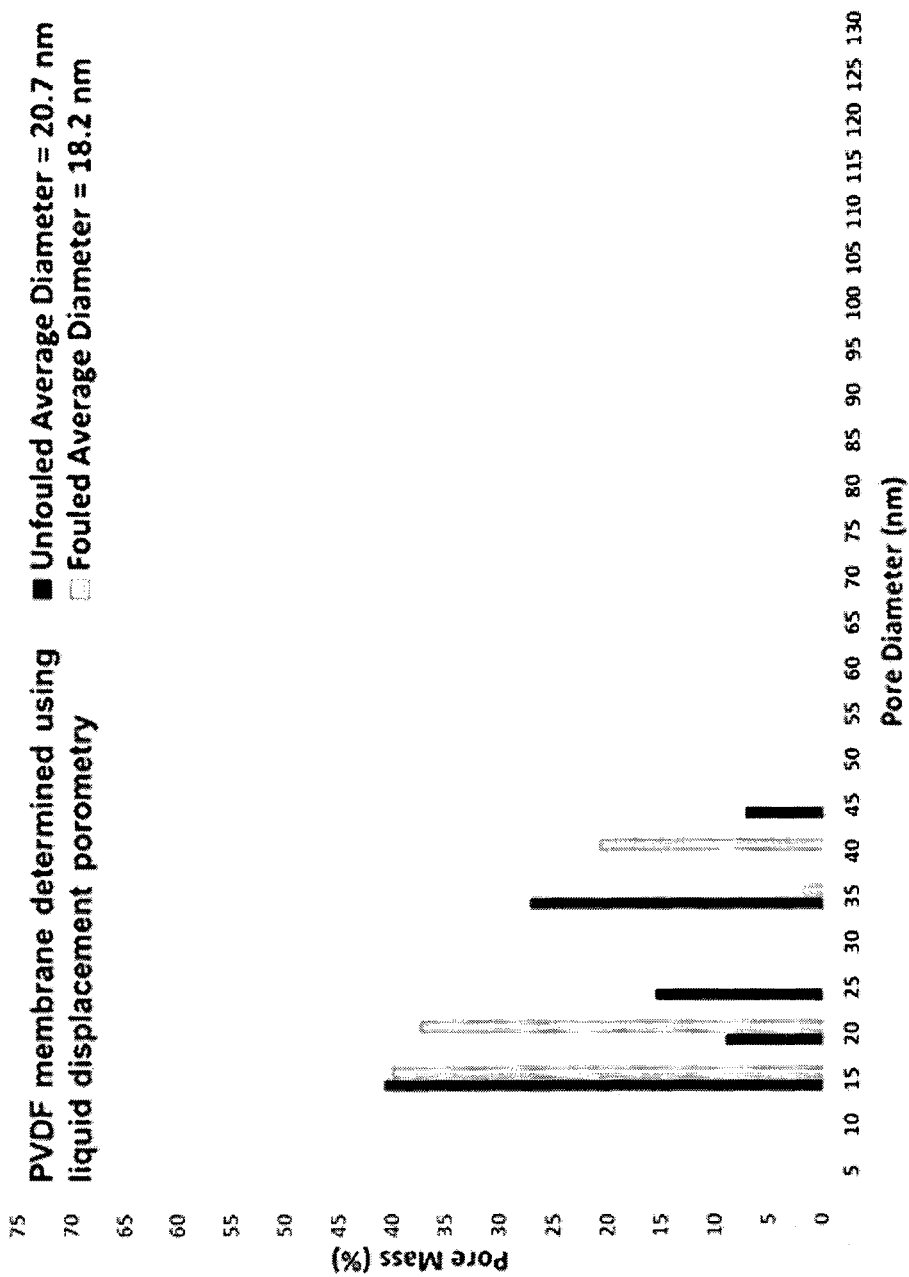
FIG. 10C shows the results of the pore-size distribution (PSD) for polyvinylidene fluoride (PVDF) hollow fibers determined using liquid displacement porometry (LDP).

FIG. 10C compares the pore-size distribution (PSD) determined by liquid displacement porometry (LDP), using Galwick™ as the liquid, of unfouled and fouled polyvinylidene fluoride (PVDF) hollow fiber (HF) membranes (e.g., nominal 35 nm commercial PVDF hydrophilic hollow fiber membranes). The shift in the PSD owing to fouling may not be nearly as pronounced as seen in FIGS. 10A and 10B for the EP characterization. The flow-average pore diameters of the fouled and unfouled membranes for LDP characterization are about 20.7±3.8 nm and about 18.2±1.0 nm, respectively. However, the largest detectable pore by LDP may be almost the same for the clean and fouled membranes. This may possibly be because LDP involves flow through the pores that may have removed some of the fouling deposits. This removal of fouling deposits may be more pronounced in the larger pores since the volume flow depends on d$^4$. For this reason, LDP may be problematic for characterizing the effect of internal pore fouling on the PSD. Since EP does not involve flow through the pores, it may provide a more reliable technique for assessing the effect of internal pore fouling on the PSD.

As described above, various embodiments may employ a configuration for carrying out EP on hollow fiber membranes, whereby the fibers may be laid horizontally and slightly raised above a free standing liquid layer provided at the bottom of a chamber or test cell so as to avoid wetting artifacts. In various embodiments, the ends of the hollow fibers may be sealed, rather than having the hollow fibers compressed between the flanged assembly at the bottom of the chamber or test cell.

The analysis in various embodiments may employ the mass-transfer coefficient rather than a solution to the diffusion equation. As such, this may allow the implementation of the chamber or test cell for liquids such as water whose vapor is less dense than air, and which therefore may cause free convection mass transfer. The use of the mass-transfer coefficient may also provide an exact way to include the effects of the exit resistance to mass transfer.

In various embodiments, when working with water, a mesh made of fiberglass or another inert material that may not react with water vapor may be employed. This mesh may serve to damp or eliminate the free convection currents, thereby providing a diffusion resistance that may control the rate of evaporation. If the free convection is not damped or eliminated to the extent that a diffusive resistance controls the mass transfer, the evaporation may be too rapid, thereby causing excessive evaporative cooling and irreproducible results. Therefore, in this way, the mesh (e.g., the fiberglass) may provide the dominant resistance (e.g., in the form of diffusion resistance). While there may still be free convection in the test cell, however, the much larger diffusional resistance provided by the mesh may control the mass transfer.

In various embodiments, one or more adsorbent materials may be optimally placed in the chamber or housing of the microbalance to ensure that vapors of the volatile liquid may not build up therein, which otherwise may cause an unknown reduction in the mass-transfer driving force for evaporation.

In various embodiments, when using water as the volatile liquid, the evapoporometry characterization may be carried out in a room having a controlled low relative humidity.

Various embodiments may allow the use of volatile liquids such as water for which the vapor is less dense than air as well as liquids such as isopropyl alcohol (IPA) whose vapor is more dense than air. Characterizing the pore-size distribution of some media such as biofilms and membranes used for water treatment may necessarily require using water as the volatile liquid during the evapoporometry characterization.

In various embodiments, the relative humidity in the chamber or housing of the microbalance may be continuously measured and/or monitored. This may be necessary, for example, when water is used as the volatile liquid for evapoporometry characterization.

Various embodiments may employ a chamber or test cell whose wall may be made of Teflon or an equivalent low energy surface to ensure that the wetting liquid or the wetting liquid molecules do not wet the chamber or cell wall.

Various embodiments may be adapted to determine internal pore fouling in hollow fiber membranes.

Various embodiments may permit assessing the effectiveness of membrane cleaning protocols on mitigating internal pore fouling.

As described above, evapoporometry (EP) may be adapted for characterization of the pore-size distribution (PSD) on the outside of hollow fiber (HF) membranes by designing an appropriate chamber or test cell and developing an associated data-analysis protocol. For example, the chamber or cell design may permit using wetting liquids such as water whose vapor is less dense than air. The chamber or test cell design may adequately control the evaporation rate from the fibers and may permit the vapor at the membrane surface to be saturated with respect to the liquid in the pores from which liquid is evaporating. As described, different wetting liquids may be used for EP characterization of the same membranes.

Various embodiments may include one or more of the following features: (1) elevating the HFs slightly above the free-standing liquid layer at the bottom of the chamber or test cell may eliminate any effects associated with initially immersing them in this layer that may interfere in the PSD determination via EP; (2) a diffusional resistance may be placed in the chamber or test cell when liquids such as water are used that may cause free convection mass transfer; for example, 1 cm of fiberglass placed above the HFs may provide a mass-transfer resistance that may dominate over the mass-transfer associated with any free convection; (3) any buildup of vapor in the chamber or housing of the microbalance may be minimised or avoided by employing some adsorbent; for example, dehumidification may be employed in order to carry out EP characterization in a humid environment; or (4) the ends of the HFs may be sealed before immersing them in the volatile wetting liquid in order to minimise or avoid liquid getting into the lumen of the fiber and to minimise or avoid any evaporation of liquid on the lumen side.

As described above, the accuracy of EP for characterization of HFs may be assessed by comparing the PSD determined for commercial PVDF and PAN membranes using different wetting liquids (e.g., water and IPA) with LDP characterization and the nominal pore diameter given by the manufacturer of the membranes. The EP measurements may provide one or more of the following: (1) good corroboration between the nominal pore diameter of the PVDF membrane and the mass-average pore diameter determined by EP with IPA and water; (2) replicate runs for each liquid compare well with each other; (3) the mass-average pore diameters determined using IPA and water, when corrected for a non-zero contact angle of water on PVDF and PAN, agree within the experimental error bounds; (4) LDP provides a smaller pore diameter than EP for the PVDF membrane probably due to membrane compaction at the high pressures used in LDP; (5) LDP provides a larger average pore diameter than EP for PAN due to the inability of LDP to characterize pores smaller than 14 nm and because it gives the flow-average rather than the mass-average diameter determined by EP; (6) EP may provide a quantitative assessment of the effect of internal pore fouling vis-à-vis a shift of the PSD towards smaller pore diameters and a markedly smaller mass-average pore diameter; or (7) the PSD obtained via LDP for internal pore fouling appears to be compromised by LDP removing some of the internal pore fouling deposits and its inability to measure pores smaller than 14 nm.

Furthermore, as described above, hollow fiber (HF) membranes are used in many applications for which characterization of the pore-size distribution (PSD) may be necessary. Current techniques for determining the PSD require relatively expensive dedicated equipment. Moreover, most techniques are not applicable for characterization of fouled membranes. Evapoporometry (EP) as described herein may provide a characterization technique based on vapor-pressure depression that may detect the full spectrum of pore sizes in ultrafiltration (UF) membranes. EP may be used to determine the PSD of flat sheet membranes using water or isopropyl alcohol (IPA) as the volatile wetting test liquid. EP may also be extended to HF membranes using IPA and/or water as the test liquids (volatile liquids). Nevertheless, it should be appreciated that other volatile liquids may also be used.

As described above, using EP, the average pore diameter of the polyvinylidene fluoride (PVDF) HF membranes using IPA and water as the test liquids may be determined to be 30.2±1.4 nm and 28.9±0.3 nm, respectively. The average pore diameter using IPA and water for the polyacrylonitrile (PAN) HF membranes may be determined to be 11.8±1.0 nm and 12.4±1.0 nm, respectively. However, liquid displacement porometry (LDP) provide a markedly smaller average pore diameter of 20.7±3.8 nm for the PVDF membranes owing to compaction under displacement pressures as high as 6 MPa. LDP also provides a substantially larger average pore diameter of 26.5±1.0 nm for the PAN membranes owing to its inability to characterize pores smaller than 14 nm. Further, as described above, EP characterization of the PSD before and after fouling the PVDF membrane with humic acid and bentonite show a 38% reduction in the effective average pore diameter owing to internal pore fouling.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

The invention claimed is:

1. A method for determining at least one pore-related parameter of a porous material, the method comprising:
    supplying a volatile liquid layer comprising a first amount of volatile liquid into a chamber;
    placing a porous material comprising one or more tubular porous materials, each of the one or more tubular porous materials comprising a lumen with opposite ends of the lumen sealed, within the chamber, the porous material having pores saturated with a second amount of the volatile liquid and being spaced apart from and over the volatile liquid layer;
    determining an evaporation rate of the second amount of the volatile fluid from the pores over a period of time by measuring an effective mass of the chamber comprising a mass of the chamber, a mass of the volatile liquid layer comprising the first amount of volatile liquid, and a mass of the porous material comprising the second amount of the volatile liquid over the period of time; and
    determining at least one pore-related parameter of the porous material based on the evaporation rate,
    wherein the pore-related parameter is any one selected from a group consisting of a porosity, a pore size, a pore-size distribution, and an internal pore fouling of the porous material.

2. The method as claimed in claim 1, wherein measuring the effective mass of the chamber comprises measuring the effective mass of the chamber at a series of time intervals.

3. The method as claimed in claim 1, further comprising determining a start of a pore-liquid evaporation period prior to measuring the effective mass of the chamber.

4. The method as claimed in claim 3, wherein determining the start of a pore-liquid evaporation period comprises:
    determining a porosity of the porous material; and
    measuring, based on the determined porosity, a mass of the second amount of the volatile liquid present in the pores of the porous material.

5. The method as claimed in claim 1, further comprising:
    determining a contact angle between the porous material and the second amount of the volatile liquid present in the pores of the porous material, and
    wherein determining the at least one pore-related parameter of the porous material further comprises modifying the determined at least one pore-related parameter according to the contact angle determined.

6. The method as claimed in claim 1,
    wherein the at least one pore-related parameter is a pore-size distribution,
    wherein measuring the effective mass of the chamber comprises measuring the effective mass of the chamber at a series of time intervals to generate a plurality of instantaneous masses,
    wherein determining the at least one pore-related parameter of the porous material comprises:
    relating a respective instantaneous mass of the determined plurality of instantaneous masses to a respective pore diameter of the porous material; and
    determining the pore-size distribution based on the instantaneous masses determined and the associated pore diameters.

7. The method as claimed in claim 1, further comprising saturating the pores of the porous material with the second amount of the volatile liquid prior to placing the porous material in the chamber.

8. The method as claimed in claim 1, further comprising controlling evaporation of the second amount of the volatile liquid in the chamber.

9. The method as claimed in claim 8, wherein controlling evaporation of the second amount of the volatile liquid in the chamber comprises arranging a diffusional resistance element spaced apart from and over the porous material, wherein the diffusional resistance element is configured to resist diffusion of vapor of the second amount of the volatile liquid.

10. The method as claimed in claim 9, wherein arranging the diffusional resistance element spaced apart from and over the porous material comprises arranging a microporous membrane or a microporous filter spaced apart from and over the porous material.

11. The method as claimed in claim 9, wherein arranging the diffusional resistance element spaced apart from and over the porous material comprises arranging a covering structure spaced apart from and over the porous material, the covering structure having a hole.

12. The method as claimed in claim 9, wherein arranging the diffusional resistance element spaced apart from and over the porous material comprises arranging a layer of fiberglass within the chamber, spaced apart from and over the porous material.

13. The method as claimed in claim 1, wherein the one or more tubular porous materials comprises a plurality of tubular porous materials, and wherein the method further comprising laying the plurality of tubular porous materials side-by-side.

* * * * *